(12) United States Patent
Haviv et al.

(10) Patent No.: US 6,777,535 B1
(45) Date of Patent: Aug. 17, 2004

(54) N-ALKYLATED PEPTIDES HAVING ANTIANGIOGENIC ACTIVITY

(75) Inventors: Fortuna Haviv, Deerfield, IL (US); Jack Henkin, Highland Park, IL (US); Douglas M. Kalvin, Buffalo Grove, IL (US); Michael F. Bradley, Wadsworth, IL (US)

(73) Assignee: Abbott Laboratories, Abbott Park, IL (US)

( * ) Notice: Subject to any disclaimer, the term of this patent is extended or adjusted under 35 U.S.C. 154(b) by 240 days.

(21) Appl. No.: 09/703,233

(22) Filed: Oct. 31, 2000

Related U.S. Application Data

(60) Provisional application No. 60/166,924, filed on Nov. 22, 1999.

(51) Int. Cl.$^7$ .................................................. C07K 7/00
(52) U.S. Cl. ........................................ 530/328; 514/15
(58) Field of Search ............................ 530/328; 514/15

(56) References Cited

U.S. PATENT DOCUMENTS

| | | | |
|---|---|---|---|
| 5,190,918 A | 3/1993 | Deutch et al. | ................ 514/15 |
| 5,192,744 A | 3/1993 | Bouck et al. | ................. 514/8 |
| 5,200,397 A | 4/1993 | Deutch et al. | ................ 514/15 |
| 5,426,100 A | 6/1995 | Deutch et al. | ................ 514/15 |

FOREIGN PATENT DOCUMENTS

| | | |
|---|---|---|
| EP | 0 443 404 | 8/1991 |
| WO | 93 16716 | 9/1993 |
| WO | 97 33174 | 9/1997 |
| WO | 97 41824 | 11/1997 |
| WO | 98 41542 | 9/1998 |

OTHER PUBLICATIONS

Donoviel, et al., *J. Biological Chemistry*, vol. 263 (35), 1988, pp. 18590–18593.
Folkman, *Cancer Research*, vol. 46, 1986, pp. 467–473.
Folkman, et al., *Science*, vol. 235, 1987, pp. 442–447.
Folkman, et al., *The Journal of Biological Chemistry*, vol. 264 (12), 1989, pp. 6892–6897.
Folkman, *Journal of the National Cancer Institute*, vol. 82 (1), 1990, pp. 4–6.
Gasparini, et al., *J. Clinical Oncology*, vol. 13 (3), 1995, pp. 765–782.
Haverstick, et al., *Biochemistry*, vol. 23, 1984, pp. 5597–5603.
Hennessy, et al., *J. Cell Biology*, vol. 108, 1989, pp. 729–736.
Lawler, et al., *J. Cell Biology*, vol. 103, 1986, pp. 1635–1648.
Majack, et al., *Cell Membranes Methods–Reviews*, vol. 3, 1987, pp. 55–77.
Prescott, Ed., *Methods in Cell Biology*, vol. XIV, Academic Press, New York, N.Y., 1976, pp. 33 et seq.
Santoro, et al., *Methods in Enzymology*, vol. 144, 1987, pp. 438–446.
Tolsma, et al., *J. Cell Biol.*, vol. 122 (2), 1993, pp. 497–511.
Weidner, et al., *The New England Journal of Medicine*, vol. 324 (1), 1991, pp. 1–8.
U.S. patent application Ser. No. 09/316,888, filed May 21, 1999.
U.S. patent application Ser. No. 60/166,791, filed Nov. 22, 1999.

*Primary Examiner*—Christopher S. F. Low
*Assistant Examiner*—David Lukton
(74) *Attorney, Agent, or Firm*—Gregory W. Steele; Johanna M. Corbin; B. Gregory Dunner

(57) ABSTRACT

N-Alkylated peptides of formula (I)

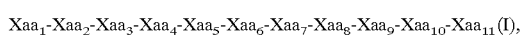

$$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Xaa_{11} \text{ (I)},$$

are useful for inhibiting angiogenesis. Also disclosed are angiogenesis-inhibiting compositions and methods of inhibiting angiogenesis in a mammal.

38 Claims, No Drawings

N-ALKYLATED PEPTIDES HAVING ANTIANGIOGENIC ACTIVITY

CROSS-REFERENCE TO RELATED APPLICATIONS

This provisional U.S. Patent Application Ser. No. 60/166,924, filed Nov. 22, 1999.

TECHNICAL FIELD

The invention relates to novel compounds having activity useful for treating conditions which arise or are exacerbated by angiogenesis, pharmaceutical compositions comprising the compounds, methods of treatment using the compounds, and methods of inhibiting angiogenesis.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions these molecules appear to maintain the microvasculature in a quiescent state (i.e., one of no capillary growth) for prolonged periods that may last for weeks, or in some cases, decades. However, when necessary, such as during wound repair, these same cells can undergo rapid proliferation and turnover within as little as five days (Folkman, J. and Shing, Y., The Journal of Biological Chemistry, 267(16): 10931–10934, and Folkman, J. and Klagsbrun, M., Science, 235: 442–447 (1987)).

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition. For example, ocular neovascularization has been implicated as the most common cause of blindness. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J., Cancer Research, 46: 467–473 (1986), Folkman, J., Journal of the National Cancer Institute, 82: 4–6 (1989)). It has been shown, for example, that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant sites, such as the liver, the lung, and the bones (Weidner, N., et. al., The New England Journal of Medicine, 324(1): 1–8 (1991)).

Several angiogenesis inhibitors are currently under development for use in treating angiogenic diseases (Gasparini, G. and Harris, A. L., J Clin Oncol 13(3): 765–782, (1995)). A number of disadvantages have been associated with many of these compounds. A potent angiogenesis inhibitor, for example suramin, can cause severe systemic toxicity in humans at doses required to reach antitumor activity. Other compounds, such as retinoids, interferons, and antiestrogens are safe for human use, but have only a weak antiangiogenic effect.

A new class of compounds having particularly effective in vitro and in vivo angiogenesis inhibiting properties, as well as a promising toxicity profile, has been described in commonly-owned U.S. patent application Ser. No. 09/316,888, filed May 21, 1999. Novel changes in position 3 of the new angiogenesis inhibitors is described in copending provisional U.S. Patent Application Ser. No. 60/166,791, filed Nov. 22, 1999. Although the compounds have demonstrated satisfactory enzymatic stability and bioavailability, it would be desirable to prepare analogs of the antiangiogenic peptides having enhanced stability against in vivo enzymatic cleavage, improved pharmacokinetics, increased water solubility, and potentially better oral bioavailability.

SUMMARY OF THE INVENTION

The present invention relates to a novel class of compounds having angiogenesis-inhibiting properties. The invention provides nona- and decapeptides wherein the nitrogen atom of at least one of the amide bonds of an amino acid residue in positions 2 through 9 of the peptide is N-alkylated. Compounds of the invention exhibit enhanced metabolic stability, improved pharmacokinetics, increased water solubility, and potentially better oral bioavailability.

In one aspect, the present invention provides a compound of formula (I)

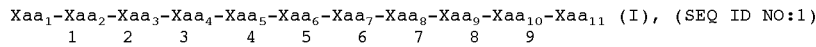

$$\text{Xaa}_1\text{-Xaa}_2\text{-Xaa}_3\text{-Xaa}_4\text{-Xaa}_5\text{-Xaa}_6\text{-Xaa}_7\text{-Xaa}_8\text{-Xaa}_9\text{-Xaa}_{10}\text{-Xaa}_{11} \quad (I), \text{ (SEQ ID NO:1)}$$
$$1 \quad 2 \quad 3 \quad 4 \quad 5 \quad 6 \quad 7 \quad 8 \quad 9$$

or a pharmaceutically acceptable salt, prodrug, ester, or solvate thereof, wherein at least one amide bond of an amino acid residue represented by $\text{Xaa}_3$, $\text{Xaa}_4$, $\text{Xaa}_5$, $\text{Xaa}_6$, $\text{Xaa}_7$, $\text{Xaa}_8$, $\text{Xaa}_9$, and $\text{Xaa}_{10}$ is N-alkylated;

$\text{Xaa}_1$ is absent or $\text{Xaa}_1$ is selected from the group consisting of hydrogen, N-methylprolyl, and an acyl group, wherein the acyl group is selected from the group consisting of
$R^1$—$(CH_2)_n$—$C(O)$—, wherein n is an integer from 0 to 8 and $R^1$ is selected from the group consisting of N-acetylamino, alkoxy, alkyl, aryl, carboxy, cycloalkenyl, cycloalkyl, heterocycle, and hydroxy; and
$R^2$—$CH_2CH_2$—O—$(CH_2CH_2O)_p$—$CH_2$—$C(O)$—, wherein p is an integer from 1 to 8 and $R^2$ is selected from the group consisting of hydrogen, N-acetylamino, and alkyl;

provided that $\text{Xaa}_1$ is absent only when $\text{Xaa}_2$ is N-$(R^3)$-prolyl;

$\text{Xaa}_2$ is an N-alkylated amino acid selected from the group consisting of N-$(R^3)$-alanyl, N-$(R^3)$-glycyl, N-$(R^3)$-norvalyl, and N-$(R^3)$-prolyl, wherein $R^3$ is $C_1$–$C_5$-alkyl; or $\text{Xaa}_2$ is an N-unalkylated amino acid selected from the group consisting of
β-alanyl,
D-alanyl,
4-aminobutyryl,
(1R,3S)-1-aminocyclopentane-3-carbonyl, (1S,3R)-1-aminocyclopentane-3-carbonyl,
(1R,4S)-1-aminocyclopent-2-ene-4-carbonyl,
(1S,4R)-1-aminocyclopent-2-ene-4-carbonyl,
asparaginyl,
3-(4-chlorophenyl)alanyl,
3-(4-cyanophenyl)alanyl,
glutaminyl,
glutamyl,
glycyl,
4-hydroxyprolyl,
3-(4-methylphenyl)alanyl,
prolyl,
seryl, and
threonyl;
Xaa$_3$ is an N-alkylated amino acid selected from the group consisting of N-(R$^3$)-alanyl, N-(R$^3$)-glycyl, N-(R$^3$)-leucyl, and N-(R$^3$)-phenylalanyl, wherein R$^3$ is as defined above; or Xaa$_3$ is an N-unalkylated amino acid selected from the group consisting of
alanyl,
(1S,3R)-1-aminocyclopentane-3-carbonyl,
(1S,4R)-1-aminocyclopent-2-ene-4-carbonyl,
asparaginyl,
aspartyl,
3-(3-cyanophenyl)alanyl,
3-(4-cyanophenyl)alanyl,
glutaminyl,
glycyl,
leucyl,
lysyl(N-epsilon-acetyl),
3-(4-methylphenyl)alanyl,
norvalyl,
prolyl, and
phenylalanyl;
Xaa$_4$ is an N-alkylated amino acid selected from the group consisting of N-(R$^3$)-alanyl, N-(R$^3$)-glycyl, N-(R$^3$)-homophenylalanyl, N-(R$^3$)-isoleucyl, N-(R$^3$)-leucyl, N-(R$^3$)-norvalyl, N-(R$^3$)-phenylalanyl, N-(R$^3$)-D-phenylalanyl, N-(R$^3$)-seryl, N-(R$^3$)-tyrosyl, N-(R$^3$)-valyl, and N-(R$^3$)-D-valyl, wherein R$^3$ is as defined above; or Xaa$_4$ is an N-unalkylated amino acid selected from the group consisting of
alanyl,
alloisoleucyl,
allylglycyl,
2-aminobutyryl,
(1R,4S)-aminocyclopent-2-ent-4-carbonyl,
asparaginyl,
aspartyl,
3-[2-(5-bromothienyl)]alanyl,
3-(3-chlorophenyl)alanyl,
3-(4-chlorophenyl)alanyl,
3-(3-cyanophenyl)alanyl,
cyclohexylalanyl,
3-(3,4-dimethoxyphenyl)alanyl,
3-(3-fluorophenyl)alanyl,
3-(4-fluorophenyl)alanyl,
glutaminyl,
glycyl,
histidyl,
homophenylalanyl,
homoseryl,
isoleucyl,
leucyl,
lysyl(N-epsilon-acetyl),
methionyl,
methionyl(sulfone),
3-(4-methylphenyl)alanyl,
3-(naphth-1-yl)alanyl,
3-(naphth-2-yl)alanyl,
noronithyl,
norvalyl,
phenyalanyl,
phenylglycyl,
prolyl,
3-(3-pyridyl)alanyl,
3-(4-thiazolyl)alanyl,
3-(2-thienyl)alanyl,
seryl,
seryl(O-benzyl),
styrylalanyl,
tryptyl,
tyrosyl,
valyl, and
D-valyl;
Xaa$_5$ is an N-alkylated amino acid selected from the group consisting of N-(R$^3$)-D-homophenylalanyl, N-(R$^3$)-D-isoleucyl, N-(R$^3$)-D-leucyl, and N-(R$^3$)-D-phenyllalanyl, wherein R$^3$ is as defined above; or Xaa$_5$ is an N-unalkylated amino acid selected from the group consisting of
D-alanyl,
alloisoleucyl,
D-alloisoleucyl,
D-2-aminobutyryl,
D-3-(4-aminophenyl)alanyl,
D-asparaginyl,
D-3-(3-benzothienyl)alanyl,
D-t-butylglycyl,
D-(chlorophenyl)alanyl,
D-citrullyl,
D-3-(3-cyanophenyl)alanyl,
D-cyclohexylalanyl,
cyclohexylglycyl,
D-cysteinyl(S-acetamidomethyl),
D-cysteinyl(S-t-butyl),
D-3-(3,4-difluorophenyl)alanyl,
D-(3,4-dimethoxyphenyl)alanyl,
D-glutaminyl,
glycyl,
D-homophenylalanyl,
D-homoseryl,
isoleucyl,
D-isoleucyl,
D-leucyl,
D-lysyl(N-epsilon-nicotinyl),
D-lysyl,
D-methionyl,
D-3-(4-methylphenyl)alanyl,
D-3-(naphth-1-yl)alanyl,
D-3-(naphth-2-yl)alanyl,
D-3-(4-nitrophenyl)alanyl,
D-norleucyl,
D-ornithyl,
D-penicillaminyl(S-acetamidomethyl),
D-penicillaminyl(S-benzyl),
D-penicillaminyl(S-methyl),
D-penicillaminyl,
D-3-(pentafluorophenyl)alanyl,
D-phenylalanyl,
D-prolyl,
D-seryl(O-benzyl),
D-seryl,
D-(2-thienyl)alanyl, D-threonyl(O-benzyl),
D-threonyl,
D-3-(3-trifluoromethylphenyl)alanyl,
D-(3,4,5-trifluorophenyl)alanyl,
D-tryptyl,
D-tyrosyl(O-ethyl),
D-tyrosyl, and
D-valyl;

$Xaa_6$ is an N-alkylated amino acid selected from the group consisting of N-($R^3$)-aspartyl, N-($R^3$)-glutamyl, N-($R^3$)-glycyl, N-($R^3$)-seryl, N-($R^3$)-threonyl, N-($R^3$)-threonyl(O-benzyl, and N-($R^3$)-tyrosyl, wherein $R^3$ is as defined above; or $Xaa_6$ is an N-unalkylated amino acid selected from the group consisting of
alanyl,
allothreonyl,
D-allothreonyl,
allylglycyl,
asparaginyl,
aspartyl,
glutaminyl,
glycyl,
histidyl,
homoseryl,
D-homoseryl,
3-(4-hydroxymethylphenyl)alanyl,
isoleucyl,
lysyl(N-epsilon-acetyl),
methionyl,
3-(naphth-2-yl)alanyl,
norvalyl,
octylglycyl,
prolyl,
3-(3-pyridyl)alanyl,
seryl,
D-seryl,
threonyl,
D-threonyl,
tryptyl,
tyrosyl, and
tyrosyl(O-methyl);

$Xaa_7$ is an N-alkylated amino acid selected from the group consisting of N-($R^3$)-alanyl, N-($R^3$)-glycyl, N-($R^3$)-isoleucyl, N-($R^3$)-leucyl, N-($R^3$)-D-leucyl, N-($R^3$)-norleucyl, N-($R^3$)-norvalyl, N-($R^3$)-seryl, N-($R^3$)-threonyl, and N-($R^3$)-valyl, wherein $R^3$ is as defined above; or $Xaa_7$ is an N-unalkylated amino acid selected from the group consisting of
alanyl,
allothreonyl,
allylglycyl,
3-(4-amidophenyl)alanyl,
2-aminobutyryl,
arginyl,
asparaginyl,
cyclohexylalanyl,
glutaminyl,
D-glutaminyl,
glycyl,
homoalanyl,
homoseryl,
4-hydroxyprolyl,
leucyl,
D-leucyl,
lysyl(N-epsilon-acetyl),
methionyl sulfone,
methionyl sulfoxide,
methionyl,
norleucyl,
norvalyl,
D-norvalyl,
octylglycyl,
ornithyl(N-delta-acetyl),
phenylalanyl,
propargylglycyl,
seryl,
D-seryl,
threonyl,
tryptyl,
tyrosyl, and
valyl;

$Xaa_8$ is an N-alkylated amino acid selected from the group consisting of N-($R^3$)-alanyl, N-($R^3$)-D-alanyl, N-($R^3$)-isoleucyl, and N-($R^3$)-leucyl, wherein $R^3$ is as defined above; or $Xaa_8$ is an N-unalkylated amino acid selected from the group consisting of
alanyl,
alloisoleucyl,
D-alloisoleucyl,
allylglycyl,
citrullyl,
glycyl,
isoleucyl,
D-isoleucyl,
leucyl,
D-leucyl,
lysyl(N-epsilon-acetyl),
D-lysyl(N-epsilon-acetyl),
methionyl,
3-(naphth-1-yl)alanyl,
norvalyl,
prolyl,
D-prolyl, and
valyl;

$Xaa_9$ is the N-alkylated amino acid N-($R^3$)-arginyl, wherein $R^3$ is as defined above; or $Xaa_9$ is an N-unalkylated amino acid selected from the group consisting of
[(4-amino-N-isopropyl)cyclohexyl]alanyl,
3-(4-amino-N-isopropylphenyl)alanyl,
arginyl($N^G N^{G'}$ diethyl),
arginyl,
D-arginyl,
citrullyl,
glutaminyl,
3-(4-guanidinophenyl)alanyl,
histidyl,
homoarginyl,
lysyl(N-epsilon-isopropyl),
lysyl(N-epsilon-nicotinyl),
lysyl,
norarginyl,
ornithyl,
ornithyl[N-delta-(2-imidazolinyl)],
ornithyl(N-delta-isopropyl), and
3-(3-pyridyl)alanyl;

$Xaa_{10}$ is an N-alkylated amino acid selected from the group consisting of N-($R^3$)-alanyl, N-($R^3$)-D-alanyl, N-($R^3$)-glycyl, N-($R^3$)-homoalanyl, and N-($R^3$)-norvalyl, wherein $R^3$ is as defined above; or $Xaa_{10}$ is an N-unalkylated amino acid selected from the group consisting of
D-alanyl,
2-aminobutyryl, D-2-aminobutyryl,
2-aminoisobutyryl,
3,4-dehydroprolyl,
4-hydroxyprolyl,
phenylalanyl,
prolyl,
D-prolyl,
1,2,3,4-tetrahydroisoquinoline-3-carbonyl, and
D-valyl; and $Xaa_{11}$ is a hydroxy group or an amino acid amide selected from the group consisting of:
alanylamide,
D-alanylamide,
alanylethylamide,
D-alanylethylamide,
azaglycylamide,
glycylamide,
glycylethylamide,
lysyl(N-epsilon-acetyl),
D-lysyl(N-epsilon-acetyl),
N-methyl-D-alanylamide,
sarcosylamide,
serylamide,
D-serylamide,
a residue represented by the formula

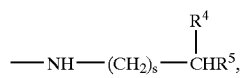

and
a group represented by the formula —NH—$R^6$;
wherein
s is an integer from 0 to 8;
$R^4$ is selected from the group consisting of hydrogen, alkyl, and a 5- to 6-membered cycloalkyl ring;
$R^5$ is selected from the group consisting of hydrogen, alkoxy, alkyl, aryl, cycloalkenyl, cycloalkyl, heterocycle, and hydroxy;
provided that s is not zero when $R^5$ is hydroxy or alkoxy; and
$R^6$ is selected from hydrogen and hydroxy.

In another aspect, the present invention provides a composition for treating a patient in need of anti-angiogenesis therapy comprising a compound of formula (I) in combination with a pharmaceutically acceptable carrier.

Yet another aspect of the present invention provides a method for treating a patient in need of anti-angiogenesis therapy comprising administering to the patient a therapeutically effective amount of a compound of formula (I).

Still yet another aspect of the present invention provides a composition for the treatment of a disease selected from cancer, arthritis, psoriasis, angiogenesis of the eye associated with infection or surgical intervention, macular degeneration, and diabetic retinopathy comprising a compound of formula (I) in combination with a pharmaceutically acceptable carrier.

In yet another aspect, the present invention provides a method of isolating a receptor from an endothelial cell comprising binding a compound of formula (I) to the receptor to form a peptide receptor complex, isolating the peptide receptor complex, and purifying the receptor.

DETAILED DESCRIPTION OF THE INVENTION

Definition of Terms

As used herein, the singular forms "a", "an", and "the" include plural reference unless the context clearly dictates otherwise.

As used in the present specification the following terms have the meanings indicated:

The term "N-acetylamino," as used herein, refers to —NHC(O)CH$_3$.

The term "acyl," as used herein, refers to an alkyl group attached to the parent molecular moiety through a carbonyl group.

The term "alkoxy," as used herein, refers to an alkyl group attached to the parent molecular moiety through an oxygen atom.

The term "alkyl," as used herein, refers to a monovalent group derived from a straight or branched chain saturated hydrocarbon by the removal of a hydrogen atom. Preferred alkyl groups for the present invention invention are alkyl groups having from one to five carbon atoms ($C_1$–$C_5$ alkyl). Alkyl groups of one to three carbon atoms ($C_1$–$C_3$ alkyl) are more preferred for the present invention.

The term "amino," as used herein, refers to —NH$_2$.

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like. The aryl groups of the present invention can be optionally substituted with one, two, three, four, or five substitutents independently selected from the group consisting of alkoxy, alkyl, carboxy, and halo.

The term "carbonyl," as used herein, refers to —C(O)—.

The term "carboxy," as used herein, refers to CO$_2$H.

The term "cycloalkenyl," as used herein, refers to a non-aromatic cyclic orbicyclic ring system having three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Examples of cycloalkenyl groups include cyclohexenyl, octahydronaphthalenyl, norbornylenyl, and the like. The cycloalkenyl groups of the present invention can be optionally substituted with one, two, three, four, or five substituents independently selected from the group consisting of alkoxy, alkyl, carboxy, halo, and hydroxy.

The term "cycloalkyl," as used herein, refers to a saturated monocyclic, bicyclic, or tricyclic hydrocarbon ring system having three to twelve carbon atoms. Examples of cycloalkyl groups include cyclopropyl, cyclopentyl, bicyclo[3.1.1]heptyl, adamantyl, and the like. The cycloalkyl groups of the present invention can be optionally substituted with one, two, three, four, or five substituents independently selected from the group consisting of alkoxy, alkyl, carboxy, halo, and hydroxy.

The term "halo," as used herein, refers to F, Cl, Br, or I.

The term "heterocycle," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocycle" also includes bicyclic groups in which the heterocycle ring is fused to an aryl group. The heterocycle groups of the present invention can be attached through a carbon atom or a nitrogen atom in the group. Examples of heterocycles include, but are not limited to, furyl, thienyl, pyrrolyl, pyrrolidinyl, oxazolyl, thiazolyl, imidazolyl, imidazolinyl, pyrazolyl, isoxazolyl, isothiazolyl, piperidinyl, morpholinyl, thiomorpholinyl, piperazinyl, pyridinyl, indolyl, indolinyl, benzothienyl, and the like. The heterocycle groups of the present invention can be optionally substituted with one, two, three, or four substituents independently selected from the group consisting of alkoxy, alkyl, carboxy, and halo.

The term "hydroxy," as used herein, refers to —OH.

The term "nicotinyl," as used herein, refers to the acyl group derived from nicotinic acid, i.e. pyridine-3-carboxylic acid. The term "2-Me-nicotinyl" or "2-methylnicotinyl" refers to a nicotinyl moiety substituted with a methyl group at the carbon adjacent to the nitrogen atom in the 2-position.

The term "nitrogen protecting group" or "N-protecting group," as used herein, refers to an easily removable group which is known in the art to protect an amino group against undesirable reaction during synthetic procedures and to be selectively removable. The use of nitrogen protecting groups is well known in the art for protecting groups against undesirable reactions during a synthetic procedure and many such protecting groups are known (see, for example, T. H. Greene and P. G. M. Wuts, Protective Groups in Organic Synthesis, 2nd edition, John Wiley & Sons, New York (1991). Examples of N-protecting groups include, are not limited to, acyl groups including acetyl, trifluoroacetyl, acylisothiocyanate, aminocaproyl, benzoyl and the like, and acyloxy groups, including t-butyloxycarbonyl (Boc) and carbobenzyloxy (Cbz), 9-fluorenylmethoxycarbonyl (Fmoc), and the like.

The term "pharmaceutically acceptable ester," as used herein, refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than six carbon atoms. Examples of particular esters include formates, acetates, propionates, butyrates, acrylates and ethylsuccinates.

The term "pharmaceutically acceptable prodrugs," as used herein, refers to those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "pharmaceutically acceptable solvate," as used herein, refers to an aggregate that comprises one or more molecules of the solute, such as a compound of formula (I), with one or more molecules of solvent.

The term "receptor," as used herein, refers to chemical groups or molecules on the cell surface or in the cell interior that have an affinity for a specific chemical group or molecule. Isolation of receptors relevant to the antiangiogenic activity of the peptide of the invention can provide useful diagnostic tools.

The term "shikimyl," as used herein, refers to the acyl residue derived from shikimic acid or [3R-(3α,4α,5β)-3,4,5-trihydroxy]-1-cyclohexene-1-carboxylic acid. A "dihydroshikimyl" group denotes the fully saturated analog of shikimic acid.

The term "succinyl," as used herein, refers to the acyl residue derived from succinic acid or (1,4-dioxobutyl)-1-carboxylic acid.

Unless indicated otherwise by a "D-" prefix, e.g. D-Ala or N-Me-D-Ile, the stereochemistry of the α-carbon of the amino acids and aminoacyl residues in peptides described in this specification and the appended claims is the natural or "L" configuration. The Cahn-Ingold-Prelog "R" and "S" designations are used to specify the stereochemistry of chiral centers in certain acyl substituents at the N-terminus of the peptides of this invention. The designation "R,S" is meant to indicate a racemic mixture of the two enantiomeric forms. This nomenclature follows that described in R. S. Cahn, et al., *Angew. Chem. Int. Ed. Engl.*, 5, 385–415 (1966).

All peptide sequences are written according to the generally accepted convention whereby the α-N-terminal amino acid residue is on the left and the α-C-terminal is on the right. As used herein, the term "α-N-terminal" refers to the free α-amino group of an amino acid in a peptide, and the term "α-C-terminal" refers to the free α-carboxylic acid terminus of an amino acid in a peptide.

For the most part, the names on naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids Recommendations, 1974)" Biochemistry, 14(2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

| Abbreviation | Definition |
|---|---|
| N-Ac-Sar | N-acetylsarcosyl |
| Ala | alanyl |
| β-Ala | β-alanyl |
| AlaNH$_2$ | alanylamide |
| AlaNH-ethyl | alanylethylamide |
| alloIle | alloisoleucyl |
| alloThr | allothreonyl |
| alloThr(t-Bu) | allothreonyl(O-t-butyl) |
| Allylgly | allyglycyl |
| 4-AmdPheAla | 3-(4-amidophenyl)alanyl |
| 2-Ambut | 2-aminobutyryl |
| 4-Ambut | 4-aminobutyryl |
| (1R,3S)-AmCyCO | (1R,3S)-1-aminocyclopentane-3-carbonyl |
| (1S,3R)-AmCyCO | (1S,3R)-1-aminocyclopentane-3-carbonyl |
| (1R,4S)-AmCyeCO | (1R,4S)-1-aminocyclopent-2-ene-4-carbonyl |
| (1S,4R)-AmCyeCO | (1S,4R)-1-aminocyclopent-2-ene-4-carbonyl |
| 2-Amisobut | 2-aminoisobutyryl |
| 4-AmIspCha | [(4-amino-N-isopropyl)cyclohexyl]alanyl |
| 4-AmIspPheAla | 3-(4-amino-N-isopropylphenyl)alanyl |
| 4-AmPheAla | 3-(4-aminophenyl)alanyl |
| Arg | arginyl |
| Arg(diethyl) | arginyl(N$^G$N$^{G'}$ diethyl) |
| Asn | asparaginyl |
| Asn(Trt) | asparaginyl(trityl) |
| AzaGlyNH$_2$ | azaglycylamide |
| 3-BzlThiAla | 3-(3-benzothienyl)alanyl |
| 5-BrThiAla | 3-[2-(5-bromothienyl)]alanyl |
| Gly(t-Bu) | t-butylglycyl |
| 3-ClPheAla | 3-(3-chlorophenyl)alanyl |
| 4-ClPheAla | 3-(4-chlorophenyl)alanyl |
| Cit | citrullyl |
| 3-CNPheAla | 3-(3-cyanophenyl)alanyl |
| 4-CNPheAla | 3-(4-cyanophenyl)alanyl |
| Cha | cyclohexylalanyl |
| Chg | cyclohexylglycyl |
| Cys | cysteinyl |
| Cys(acme) | cysteinyl(S-acetamidomethyl) |
| Cys(t-Bu) | cysteinyl(S-t-butyl) |
| dePro | 3,4-dehydroprolyl |
| 3,4-diFPheAla | 3-(3,4-difluorophenyl)alanyl |
| 3,4-diOMe-PheAla | 3-(3,4-dimethoxyphenyl)alanyl |
| Fmoc | 9-fluorenylmethyloxycarbonyl |
| 3-FPheAla | 3-(3-fluorophenyl)alanyl |
| 4-FPheAla | 3-(4-fluorophenyl)alanyl |
| Gln | glutaminyl |
| Gln(Trt) | glutaminyl(trityl) |
| GlyNH$_2$ | glycylamide |
| GlyNH-ethyl | glycylethylamide |
| 4-GuPheAla | 3-(4-guanidinophenyl)alanyl |
| Hala | homoalanyl |
| Harg | homoarginine |
| His | histidyl |

TABLE 1-continued

| Abbreviation | Definition |
|---|---|
| HpheAla | homophenylalanyl |
| Hser | homoseryl |
| 4-OHMePheAla | 3-(4-hydroxymethylphenyl)alanyl |
| 4-OHPro | 4-hydroxyprolyl |
| Ile | isoleucyl |
| Leu | leucyl |
| Lys | lysyl |
| Lys(Ac) | lysyl(N-epsilon-acetyl) |
| Lys(Isp) | lysyl(N-epsilon-isopropyl) |
| Lys(Nic) | lysyl(N-epsilon-nicotinyl) |
| Met | methionyl |
| Met(O$_2$) | methionyl(sulfone) |
| Met(O) | methionyl(sulfoxide) |
| N-MeArg(Mtr) | (N$^G$-4-methoxy-2,3,6-trimethylbenzenesulfonyl)arginyl |
| N-MeAla | N-methylalanyl |
| N-MeAlaNH$_2$ | N-methylalanylamide |
| N-MeAlaNH-ethyl | N-methylalanyl ethylamide |
| N-MeAsp | N-methylaspartyl |
| N-MeAsp(t-Bu) | N-methylaspartyl(S-t-butyl) |
| N-MeGlu | N-methylglutamyl |
| N-MeGlu(t-Bu) | N-methylglutamyl(S-t-butyl) |
| N-MeIle | N-methylisoleucyl |
| N-MeLeu | N-methylleucyl |
| N-MeNle | N-methylnorleucyl |
| N-MeNva | N-methylnorvalyl |
| N-MeNvaNH-ethyl | N-methylnorvalyl ethylamide |
| 4-MePheAla | 3-(4-methylphenyl)alanyl |
| N-MePheAla | N-methylphenylalanyl |
| N-MePro | N-methylprolyl |
| N-MeSer(t-Bu) | N-methylseryl(O-t-butyl) |
| N-MeThr(Bzl) | N-methylthreonyl(O-benzyl) |
| N-MeThr(t-Bu) | N-methylthreonyl(O-t-butyl) |
| N-MeTyr | N-methyltyrosyl |
| N-MeTyr(t-Bu) | N-methyltyrosyl(O-t-butyl) |
| N-MeVal | N-methylvalyl |
| 1-Nal | 3-(naphth-1-yl)alanyl |
| 2-Nal | 3-(naphth-2-yl)alanyl |
| 4-NO$_2$PheAla | 3-(4-nitrophenyl)alanyl |
| Narg | norarginyl |
| Nle | norleucyl |
| Nor | norornithyl |
| Nva | norvalyl |
| octylgly | octylglycyl |
| Orn | ornithyl |
| Orn(Ac) | ornityl(N-delta-acetyl) |
| Orn(Im) | ornithyl[N-delta-(2-imidazolinyl)] |
| Orn(Isp) | ornithyl(N-delta-isopropyl) |
| Pen | penicillaminyl |
| Pen(Sacme) | penicillaminyl(S-acetamidomethyl) |
| Pen(SBzl) | penicillaminyl(S-benzyl) |
| Pen(SMe) | penicillaminyl(S-methyl) |
| 3-PentaFPheAla | 3-(pentafluorophenyl)alanyl |
| Arg(Pmc) | (N$^G$-2,2,5,7,8-pentamethyl-chroman-6-sulfonyl)arginyl |
| PheAla | phenylalanyl |
| PheGly | phenylglycyl |
| Pro | prolyl |
| ProNH-ethyl | prolyl ethylamide |
| Propgly | propargylglycyl |
| 3-PyrAla | 3-(3-pyridyl)alanyl |
| Sar | sarcosyl |
| SarNH$_2$ | sarcosylamide |
| SarNH-ethyl | sarcosyl ethylamide |
| Ser | seryl |
| SerNH$_2$ | serylamide |
| Ser(Bzl) | seryl(O-benzyl) |
| Ser(t-Bu) | seryl(O-t-butyl) |
| StyAla | styrylalanyl |
| Tic | 1,2,3,4-tetrahydroisoquinoline-3-carbonyl |
| 4-ThzAla | 3-(4-thiazolyl)alanyl |
| 2-ThiAla | 3-(2-thienyl)alanyl |
| Thr | threonyl |
| Thr(Bzl) | threonyl(O-benzyl) |
| Thr(t-Bu) | threonyl(O-t-butyl) |
| 3-CF$_3$PheAla | 3-(3-trifluoromethylphenyl)alanyl |
| 3,4,5-TriFPheAla | 3-(3,4,5-trifluorophenyl)alanyl |

TABLE 1-continued

| Abbreviation | Definition |
| --- | --- |
| Tyr | tyrosyl |
| Tyr(t-Bu) | tyrosyl(O-t-butyl) |
| Tyr(Et) | tyrosyl(O-ethyl) |
| Tyr(Me) | tyrosyl(O-methyl) |
| Val | valyl |

When not found in the table above, nomenclature and abbreviations may be further clarified by reference to the Calbiochem-Novabiochem Corp. 1999 *Catalog and Peptide Synthesis Handbook* or the Chem-Impex International, Inc. *Tools for Peptide & Solid Phase Synthesis* 1998–1999 Catalogue.

In one aspect, the present invention relates to compounds of formula (I), wherein $Xaa_2$–$Xaa_{10}$ each represent an amino acyl residue; $Xaa_1$ may be absent or $Xaa_1$ is hydrogen, N-methylprolyl, or an acyl group; and $Xaa_{11}$ is a hydroxy group, an amino acid amide, or an amino residue. The amino acyl residues represented by $Xaa_2$–$Xaa_{10}$ can have an N-alkylated or an N-unalkylated amide bond. At least one of the amide bonds on a residue represented by $Xaa_3$, $Xaa_4$, $Xaa_5$, $Xaa_6$, $Xaa_7$, $Xaa_8$, $Xaa_9$, or $Xaa_{10}$ is N-alkylated.

$Xaa_1$ is absent or is selected from the group consisting of hydrogen; N-methylprolyl; $R^1$—$(CH_2)_n$—$C(O)$—, wherein n is an integer from 0 to 8 and $R^1$ is selected from the group consisting of N-acetylamino, alkoxy, alkyl, aryl, carboxy, cycloalkenyl, cycloalkyl, heterocycle, and hydroxy; and $R^2$—$CH_2CH_2$—$O$—$(CH_2CH_2O)_p$—$CH_2$—$C(O)$—, wherein p is an integer from 1 to 8 and $R^2$ is selected from the group consisting of hydrogen, N-acetylamino, and alkyl. Preferably, $Xaa_1$ is absent or is selected from the group consisting of acetyl, N-methylprolyl, and succinyl.

Amino acyl residues suitable for the $Xaa_2$ position include N-methylalanyl, sarcosyl, N-ethylglycyl, N-methylnorvalyl, N-methylprolyl,β-alanyl, D-alanyl, 4-aminobutyryl, (1R, 3S)-1-aminocyclopentane-3-carbonyl, (1S,3R)-1-aminocyclopentane-3-carbonyl, (1R,4S)-1-aminocyclopent-2-ene-4-carbonyl, (1S,4R)-1-aminocyclopent-2-ene-4-carbonyl, asparaginyl, 3-(4-chlorophenyl)alanyl, 3-(4-cyanophenyl)alanyl, glutaminyl, glutamyl, glycyl, 4-hydroxyprolyl, 3-(4-methylphenyl)alanyl, prolyl, seryl, and threonyl. When $Xaa_2$ is an N-alkylated prolyl residue, $Xaa_1$ is absent. Preferably, $Xaa_2$ is an amino acyl residue selected from the group consisting of sarcosyl and N-methylprolyl.

Suitable amino acyl residues for $Xaa_3$ include N-methylalanyl, sarcosyl, N-methylleucyl, N-methylphenylalanyl, alanyl, (1S,3R)-1-aminocyclopentane-3-carbonyl, (1S,4R)-1-aminocyclopent-2-ene-4-carbonyl, asparaginyl, aspartyl, 3-(3-cyanophenyl)alanyl, 3-(4-cyanophenyl)alanyl, glutaminyl, glycyl, leucyl, lysyl(N-epsilon-acetyl), 3-(4-methylphenyl)alanyl, norvalyl, prolyl, and phenylalanyl. The preferred amino acid residues for $Xaa_3$ are N-methylalanyl and glycyl.

The N-alkylated residues suitable for $Xaa_4$ include N-methylalanyl, sarcosyl, N-methylhomophenylalanyl, N-methylisoleucyl, N-methylleucyl, N-methylnorvalyl, N-methylphenylalanyl, N-methyl-D-phenylalanyl, N-methylseryl, N-methyltyrosyl, N-methylvalyl, and N-methyl-D-valyl. N-Unalkylated amino acyl residues suitable for $Xaa_1$ are alanyl, alloisoleucyl, allylglycyl, 2-aminobutyryl, (1R,4S)-aminocyclopent-2-ene-4-carbonyl, asparaginyl, aspartyl, 3-[2-(5-bromothienyl)]alanyl, 3-(3-chlorophenyl)alanyl, 3-(4-chlorophenyl)alanyl, 3-(3-cyanophenyl)alanyl, cyclohexylalanyl, 3-(3,4-dimethoxyphenyl)alanyl, 3-(3-fluorophenyl)alanyl, 3-(4-fluorophenylalanyl), glutaminyl, glycyl, histidyl, homophenylalanyl, homoseryl, isoleucyl, leucyl, lysyl(N-epsilon-acetyl), methionyl, methionyl(sulfone), 3-(4-methylphenyl)alanyl, 3-(naphth-1-yl)alanyl, 3-(naphth-2-yl)alanyl, norornithyl, norvalyl, phenylalanyl, phenylglycyl, prolyl, 3-(3-pyridyl)alanyl, 3-(4-thiazolyl)alanyl, 3-(2-thienyl)alanyl, seryl, seryl(O-benzyl), styrylalanyl, tryptyl, tyrosyl, valyl, and D-valyl. Preferred amino acyl residues for $Xaa_4$ are N-methylalanyl, N-methylisoleucyl, N-methylleucyl, N-methylnorvalyl, N-methylphenylalanyl, N-methyl-D-phenylalanyl, N-methylvalyl, N-methyl-D-valyl, asparaginyl, glutaminyl, isoleucyl, phenylalanyl, and valyl.

The N-alkylated amino acyl residues suitable for $Xaa_5$ are N-methyl-D-homophenylalanyl, N-methyl-D-isoleucyl, N-methyl-D-leucyl, and N-$(R^3)$-D-phenylalanyl. N-unalkylated amino acyl residues suitable for $Xaa_5$ are D-alanyl, alloisoleucyl, D-alloisoleucyl, D-2-aminobutyryl, D-3-(4-aminophenyl)alanyl, D-asparaginyl, D-3-(3-benzothienyl)alanyl, D-t-butylglycyl, D-(4-chlorophenyl)alanyl, D-citrullyl, D-3-(3-cyanophenyl)alanyl, D-cyclohexylalanyl, cyclohexylglycyl, D-cysteinyl(S-acetamidomethyl), D-cysteinyl(S-t-butyl), D-3-(3,4-difluorophenyl)alanyl, D-(3,4-dimethoxyphenyl)alanyl, D-glutaminyl, glycyl, D-homophenylalanyl, D-homoseryl, isoleucyl, D-isoleucyl, D-leucyl, D-lysyl, D-lysyl(N-epsilon-nicotinyl), D-methionyl, D-3-(4-methylphenyl)alanyl, D-3-(naphth-1-yl)alanyl, D-3-(naphth-2-yl), D-3-(4-nitropheny)alanyl, D-norleucyl, D-ornithyl, D-penicillaminyl, D-penicillaminyl(S-acetamidomethyl), D-penicillaminyl(O-benzyl), D-penicillaminyl(S-methyl), D-3-(pentafluorophenyl)alanyl, D-phenylalanyl, D-prolyl, D-seryl, D-seryl(O-benzyl), D-(2-thienyl)alanyl, D-threonyl, D-threonyl(O-benzyl), D-3-(3-trifluoromethylphenyl)alanyl, D-(3,4,5-trifluorophenyl)alanyl, D-tryptyl, D-tyrosyl, D-tyrosyl(ethyl), and D-valyl. The amino acyl residues preferred for $Xaa_5$ are N-methyl-D-leucyl, D-alloisolcucyl, D-isoleucyl, D-leucyl, D-homophenylalanyl, and D-penacillaminyl(S-methyl).

Examples of N-alkylated amino acids suitable for $Xaa_6$ are N-methylaspartyl, N-methylglutamyl, sarcosyl, N-methylseryl, N-methylthreonyl, N-methylthreonyl(O-benzyl), and N-methyltyrosyl. N-unalkylated amino acyl residues suitable for $Xaa_6$ are alanyl, allothreonyl, D-allothreonyl, allylglycyl, glutaminyl, glycyl, histidyl, homoseryl, D-homoseryl, 3-(4-hydroxymethylphenyl)alanyl, isoleucyl, lysyl(N-epsilon-acetyl), methionyl, 3-(naphth-2-yl)alanyl, norvalyl, octylglycyl, prolyl, 3-(3-pyridyl)alanyl, seryl, D-seryl, threonyl, D-threonyl, tryptyl, tyrosyl, and tyrosyl(O-methyl). The preferred amino acyl residues for $Xaa_6$ are N-methylaspartyl, N-methylglutamyl, sarcosyl, N-methylseryl, N-methyltyrosyl, N-methylthreonyl(O-benzyl), allothreonyl, seryl, threonyl, and tyrosyl.

N-Alkylated amino acyl residues suitable for $Xaa_7$ are N-methylalanyl, sarcosyl, N-methylisoleucyl, N-methylleucyl, N-methyl-D-leucyl, N-methylnorleucyl, N-methylnorvalyl, N-methylseryl, N-methylthreonyl, and N-methylvalyl. The N-unalkylated amino acyl residues suitable for $Xaa_7$ are alanyl, allothreonyl, allylglycyl, 3-(4-amidophenyl)alanyl, 2-aminobutyryl, arginyl, asparaginyl, cyclohexylalanyl, glutaminyl, D-glutaminyl, glycyl, homoalanyl, homoseryl, 4-hydroxyprolyl, leucyl, D-leucyl, lysyl(N-epsilon-acetyl), methionyl, methionyl sulfone, methionyl sulfoxide, norleucyl, norvalyl, D-norvalyl, octylglycyl, ornithyl(N-delta-acetyl), phenylalanyl, propargylglycyl, seryl, D-seryl, threonyl, tryptyl, tyrosyl, and valyl. Preferably, the amino acyl residue for $Xaa_7$ is selected from the group consisting of N-methylalanyl, sarcosyl, N-methylisoleucyl, N-methylleucyl, N-methyl-D-leucyl, N-methylnorleucyl, N-methylnorvalyl, N-methylseryl, N-methylthreonyl, N-methylvalyl, norleucyl, norvalyl, and seryl.

Suitable N-alkyl amino acyl residues for $Xaa_8$ include N-methylalanyl, N-methyl-D-alanyl, N-methylisoleucyl, and N-methylleucyl. N-Unalkylated amino acyl residues suitable for $Xaa_8$ include alanyl, alloisoleucyl, D-alloisoleucyl, allylglycyl, citrullyl, glycyl, isoleucyl, D-isoleucyl, leucyl, D-leucyl, lysyl(N-epsilon-acetyl), D-lysyl(N-epsilon-acetyl), methionyl, 3-(naphth-1-yl) alanyl, norvalyl, prolyl, D-prolyl, and valyl. Preferably, the amino acyl residue for $Xaa_8$ is selected from the group consisting of N-methylalanyl, N-methyl-D-alanyl, N-methylisoleucyl, N-methylleucyl, isoleucyl, D-isoleucyl, and D-lysyl(N-epsilon-acetyl).

One of the N-alkylated amino acyl residues suitable for $Xaa_9$ is N-methylarginyl. N-Unalkylated amino acyl residues for $Xaa_9$ are selected from the group consisting of [(4-amino-N-isopropyl)cyclohexyl]alanyl, 3-(4-amino-N-isopropylphenyl)alanyl, arginyl, arginyl($N^G N^{G'}$ diethyl), citrullyl, glutaminyl, 3-(4-guanidinophenyl)alanyl, histidyl, homoarginyl, lysyl(N-epsilon-isopropyl), lysyl(N-epsilon-nicotinyl), lysyl, norarginyl, ornithyl, ornithyl(N-delta-imidazolinyl), ornithyl(N-delta-isopropyl), and 3-(3-pyridyl)alanyl. Preferred amino acyl residues for $Xaa_9$ are arginyl and N-methylarginyl.

N-Alkylated amino acids suitable for the $Xaa_{10}$ position include N-methylalanyl, N-methyl-D-alanyl, sarcosyl, N-methylhomoalanyl, and N-methylnorvalyl. Other residues suitable for $Xaa_{10}$ include D-alanyl, 2-aminoburyryl, D-2-aminobutyryl, 2-aminoisobtyryl, 3,4-dehydroprolyl, 4-hydroxyprolyl, phenylalanyl, prolyl, D-prolyl, 1,2,3,4-tetrahydroisoquinoline-3-carbonyl, and D-valyl. The amino acyl residues preferred for $Xaa_{10}$ are N-methylalanyl, sarcosyl, N-methylnorvalyl, and prolyl.

Preferably, one or two residues selected from $Xaa_3$, $Xaa_4$, $Xaa_5$, $Xaa_6$, $Xaa_7$, $Xaa_8$, $Xaa_9$ and $Xaa_{10}$ has an N-alkylated amino acyl residue. The more preferred compounds of the invention have one N-alkylated amide bond on an amino acyl residue not including $Xaa_1$, as represented by $Xaa_3$, $Xaa_4$, $Xaa_5$, $Xaa_6$, $Xaa_7$, $Xaa_8$, $Xaa_9$ or $Xaa_{10}$.

$Xaa_{11}$ is a hydroxy group or an amino acid amide selected from the group consisting of alanylamide, D-alanylamide, alanylethylamide, D-alanylethylamide, azaglycylamide, glycylamide, glycylethylamide, lysyl(N-epsilon-acetyl), D-lysyl(N-epsilon-acetyl), N-methyl-D-alanylamide, sarcosylamide, serylamide, and D-serylamide; or $Xaa_{11}$ is a group represented by the formula

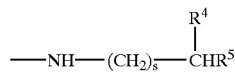

or a group represented by the formula —NH—$R^6$, wherein s is an integer selected from 0 to 8; $R^4$ is selected from hydrogen, alkyl, and a 5- to 6-membered cycloalkyl ring; $R^5$ is selected from the group consisting of hydrogen, alkoxy, alkyl, aryl, cycloalkenyl, cycloalkyl, heterocycle, and hydroxy, provided that s is not zero when $R^5$ is hydroxy or alkoxy; and $R^6$ is selected from hydrogen and hydroxy. The preferred $Xaa_{11}$ groups for modifying the C-terminus of the invention are NH-ethyl and D-alanylamide.

Compositions

The compounds of the invention, including not limited to those specified in the examples, possess anti-angiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e. chloromas, plasmacytomas and the plaques and tumors of mycosis fungosides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including not limited to intestinal adhesions, Crohn's disease, atherosclerosis, scleroderma, and hypertrophic scars, i.e. keloids. Another use is as a birth control agent, by inhibiting ovulation and establishment of the placenta. The compounds of the invention are also useful in the treatment of diseases that have angiogenesis as a pathologic consequence such as cat scratch disease (*Rochele minutesalia quintosa*) and ulcers (*Helicobacter pylori*). The compounds of the invention are also useful to reduce bleeding by administration prior to surgery, especially for the treatment of resectable tumors.

The compounds of the invention may be used in combination with other compositions and procedures for the treatment of diseases. For example, a tumor may be treated conventionally with surgery, radiation or chemotherapy combined with a peptide of the present invention and then a peptide of the present invention may be subsequently administered to the patient to extend the dormancy of micrometastases and to stabilize and inhibit the growth of any residual primary tumor. Additionally, the compounds of the invention may be combined with pharmaceutically acceptable excipients, and optionally sustained-release matrices, such as biodegradable polymers, to form therapeutic compositions.

A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

When used in the above or other treatments, a therapeutically effective amount of one of the compounds of the present invention may be employed in pure form or, where such forms exist, in pharmaceutically acceptable salt form. By a "therapeutically effective amount" of the compound of the invention is meant a sufficient amount of the compound to treat an angiogenic disease, (for example, to limit tumor growth or to slow or block tumor metastasis) at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved.

Alternatively, a compound of the present invention may be administered as pharmaceutical compositions containing the compound of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters), poly (anhydrides), and (poly)glycols, such as PEG. Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient dcs not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds of the invention may be injected directly into the vitreous and aqueous humour.

Compositions for rectal or vaginal administration are preferably suppositories which may be prepared by mixing the compounds of this invention with suitable non-irritating excipients or carriers such as cocoa butter, polyethylene glycol or a suppository wax which are solid at room temperature liquid at body temperature and therefore melt in the rectum or vaginal cavity and release the active compound.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

While the compounds of the invention can be administered as the sole active pharmaceutical agent, they may also be used in combination with one or more agents which are conventionally administered to patients for treating angiogenic diseases. For example, the compounds of the invention are effective over the short term to make tumors more sensitive to traditional cytotoxic therapies such as chemicals and radiation. The compounds of the invention also enhance the effectiveness of existing cytotoxic adjuvant anti-cancer therapies. The compounds of the invention may also be combined with other antiangiogenic agents to enhance their effectiveness, or combined with other antiangiogenic agents and administered togdiethyl ether with other cytotoxic agents. In particular, when used in the treatment of solid tumors, compounds of the invention may be administered with IL-12, retinoids, interferons, angiostatin, endostatin, thalidomide, thrombospondin-1, thrombospondin-2, captopryl, angioinhibins, TNP-470, pentosan polysulfate, platelet factor 4, LM-609, SU-5416, CM-101, Tecogalan, plasminogen-K-5, vasostatin, vitaxin, vasculostatin, squalamine, marimastat or other MMP inhibitors, antineoplastic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, cisplatin, taxol, etoposidelmechlorethamine, vincristine, prednisone and procarbazine), vincristine, vinblastine, and the like as well as with radiation.

Total daily dose of the compositions of the invention to be administered to a human or other mammal host in single or divided doses may be in amounts, for example, from 0.0001 to 300 mg/kg body weight daily and more usually 1 to 300 mg/kg body weight.

It will be understood that agents which can be combined with the compound of the present invention for the inhibition, treatment or prophylaxis of angiogenic diseases are not limited to those listed above, include in principle any agents useful for the treatment or prophylaxis of angiogenic diseases.

The peptides of the invention may be used for the development of affinity columns for isolation of receptors relevant to the antiangiogenic activity of the peptide of the invention, e.g. TSP-1 receptor, in, for example, cultured endothelial cells. As is known in the art, isolation and purification of the receptor may be followed by amino acid sequencing to identify and isolate polynucleotides which encode the receptor. Recombinant expression of this receptor would allow greater amounts of receptor to be produced, e.g. to produce a sufficient quantity for use in high throughput screening assays to identify other angiogenesis inhibitors.

Determination of Biological Activity

In Vitro Assay for Angiogenic Activity

The human microvascular endothelial (HMVEC) migration assay was run according to the procedure of S. S. Tolsma, O. V. Volpert, D. J. Good, W. F. Frazier, P. J. Polverini and N. Bouck, J. Cell Biol. 122, 497–511 (1993).

The HMVEC migration assay was carried out using Human Microvascular Endothelial Cells-Dermal (single donor) and Human Microvascular Endothelial Cells, (neonatal). The BCE or HMVEC cells were starved overnight in DME containing 0.1% bovine serum albumin (BSA). Cells were then harvested with trypsin and resuspended in DME with 0.1% BSA at a concentration of $1.5 \times 10^6$ cells per mL. Cells were added to the bottom of a 48 well modified Boyden chamber (Nucleopore Corporation, Cabin John, Md). The chamber was assembled and inverted, and cells were allowed to attach for 2 hours at 37° C. to polycarbonate chemotaxis membranes (5 $\mu$m pore size) that had been soaked in 0.1% gelatin overnight and dried. The chamber was then reinverted, and test substances (total volume of 50 $\mu$L), including activators, 15 ng/mL bFGF/VEGF, were added to the wells of the upper chamber. The apparatus was incubated for 4 hours at 37° C. Membranes were recovered, fixed and stained (Diff Quick, Fisher Scientific) and the number of cells that had migrated to the upper chamber per 3 high power fields counted. Background migration to DME+0.1 BSA was subtracted and the data reported as the number of cells migrated per 10 high power fields (400×) or, when results from multiple experiments were combined, as the percent inhibition of migration compared to a positive control.

Representative compounds described in Examples 1 to 109 inhibited human endothelial cell migration in the above assay by at least 50% inhibition when tested at concentrations of 100 nM. Preferred compounds inhibited human endothelial cell migration by at least 51% when tested at concentrations of 10 nM, and more preferred compounds inhibited human endothelial cell migration by at least 51% at concentrations of 1 nM.

Synthesis of the Peptides

The polypeptides of the present invention may be synthesized by many techniques that are known to those skilled in the art. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

Reagents, resins, amino acids, and amino acid derivatives are commercially available and can be purchased from Chem-Impex International, Inc. (Wood Dale, Ill., U.S.A.) or Calbiochem-Novabiochem Corp. (San Diego, Calif., U.S.A.) unless otherwise noted herein.

In general, these methods comprise the sequential addition of one or more amino acids or suitably protected amino acids to a growing peptide chain. Normally, either the amino or carboxy group of the first amino acid is protected by a suitable protecting group. The protected or derivatized amino acid can then be either attached to an inert solid support or utilized in solution by adding the next amino acid in the sequence having the complimentary (amino or carboxy) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis.

In this particularly preferred method the α-amino function is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are 9-fluorenylmethyloxycarbonyl (Fmoc),t-butoxycatbonyl (Boc), benzyloxycarbonyl (Cbz), biphenylisopropyloxycarbonyl,t-amyloxycarbonyl, isobornyloxycarbonyl, α,α)-dimethyl-3,5-dimethoxybenzyloxycarbonyl), O-nitrophenylsulfenyl, 2-cyano-t-butyloxycarbonyl, and the like. The 9-fluorenylmethyloxycarbonyl (Fmoc) protecting group is preferred.

Particularly preferred side chain protecting groups are: for arginine and lysine: acetyl (Ac), adamantyloxycarbonyl, benzyloxycarbonyl (Cbz),t-butyloxycarbonyl (Boc), 4-methoxybenzenesulfonyl, $N^G$4-methoxy-2,3,6-trimethylbenzenesulfonyl (Mtr), nitro, 2,2,5,7,8-pentamethylchroman-6-sulfonyl (Pmc), and p-toluenesulfonyl; for asparagine: trityl (Trt); for aspartyl: t-butyl (t-Bu); for glutamyl: t-butyl (t-Bu); for glutaminyl: trityl (Trt); for histidine: trityl (Trt), benzyl, benzyloxycarbonyl (Cbz), p-toluenesulfonyl and 2,4-dinitrophenyl; for penicillamine: methyl; for serine: t-butyl (t-Bu), benzyl and tetrahydropyranyl; for threonine: benzyl, and t-butyl (t-Bu); for tryptophan: formyl and t-butyloxycarbonyl (Boc); and for tyrosine: acetyl (Ac), benzyl,O-bromobenzyloxycarbonyl, t-butyl (t-Bu), cyclohexyl, cyclopenyl, 2,6-dichlorobenzyl, and isopropyl.

In the solid phase peptide synthesis method, the C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of C-terminal carboxy peptides is 4-hydroxymethyl-phenoxymethyl-copoly(styrene-1% divinylbenzene). The preferred solid support for C-terminal amide peptides is 4-(2',4'-dimethoxyphenyl-Fmoc-aminomethyl)phenoxy-acetamidoethyl resin available from Applied Biosystems.

The C-terminal amino acid is coupled to the resin by means of a coupling mediated by N,N'-dicyclohexylcarbodiimide (DCC), N,N'-diisopropylcarbodiimide (DIC), O-(7-azabenzotriazol-1-yl)-1,1,3,3-tetramethyluronium hexafluorophoshpate] (HATU), or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), for about 1 to about 24 hours at a temperature of between 10° C. and 50° C. in a solvent such as dichloromethane or DMF.

When the solid support is 4-(2',4'-dimethoxyphenyl-Fmoc-aminomethyl)-phenoxyacetamidoethyl resin, the Fmoc group is cleaved with a secondary amine, preferably piperidine, prior to coupling with the C-terminal amino acid as described above. The preferred reagents used in the coupling to the deprotected 4-(2',4'-dimethoxyphenyl-Fmoc-aminomethyl-phenoxyacetamidoethyl resin are O-benzotriazol-1-yl-N,N,N',N'-tetramethyluroniumhexafluorophosphate (HBTU, 1 equiv.) and 1-hydroxybenzotriazole (HOBT, 1 equiv.), or [O-(7-azabenzotriazol-1-yl)-1,1,3,3-tetramethyluronium hexafluorophoshpate] (HATU, 1 equiv.), in DMF.

The coupling of successive protected amino acids can be carried out in an automatic polypeptide synthesizer as is well known in the art. In a preferred embodiment, the α-amino function in the amino acids of the growing peptide chain are protected with Fmoc. The removal of the Fmoc protecting group from the N-terminal side of the growing peptide is accomplished by treatment with a secondary amine, preferably piperidine. Each protected amino acid is then introduced in about 3-fold molar excess and the coupling is preferably carried out in DMF. The coupling agent is normally O-benzotriazol-1-yl-N,N',N'-tetramethyluronium-hexafluorophosphate (HBTU, 1 equiv.) and 1-hydroxybenzotriazole (HOBT, 1 equiv.) or [O-(7-azabenzotriazol-1-yl)-1,1,3,3-tetramethyluronium hexafluorophosphate] (HATU, 1 equiv.).

At the end of the solid phase synthesis, the polypeptide is removed from the resin and deprotected, either in succession or in a single operation. Removal of the polypeptide and deprotection can be accomplished in a single operation by treating the resin-bound polypeptide with a cleavage reagent, for example trifluoroacetic acid containing thianisole, water, or ethanedithiol.

In cases wherein the C-terminus of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above.

The fully deprotected peptide is purified by a sequence of chromatographic steps employing any or all of the following types: ion exchange on a weakly basic resin in the acetate form; hydrophobic adsorption chromatography on underivitized polystyrene-divinylbenzene (for example, AMBERLITE® XAD); silica gel adsorption chromatography; ion exchange chromatography on carboxymethylcellulose; partition chromatography, e.g. on SEPHADEX® G-25, LH-20 or countercurrent distribution; high performance liquid chromatography (HPLC), especially reverse-phase HPLC on octyl- or octadecylsilyl-silica bonded phase column packing.

The foregoing may be better understood in light of the examples which are meant to describe compounds and process which can be carried out in accordance with the invention and are not intended as a limitation on the scope of the invention in any way.

Abbreviations which have been used the following examples are: NMP for N-methylpyrrolidinone; HATU for [O-(7-azabenzotriazol-1-yl)-1,1,3,3-tetramethyluronium hexafluorophosphate]; DMF for N,N-dimethylformamide, and TFA for trifluoroacetic acid.

EXAMPLE 1

N-Ac-Sar-Gly-Val-D-Ile-Thr-NMeNva-Ile-Arg-ProNH-ethyl

In the reaction vessel of an Applied Biosystems 433A peptide synthesizer was placed 0.1 mM of Fmoc-Pro-Sieber ethylamide resin. Cartridges of 1 mM amino acids were sequentially loaded. The Fastmoc 0.1 with previous peak monitoring protocol was used with the following synthetic cycle:

1. Resin solvated with NMP for about 5 minutes;
2. Resin washed with NMP for about 5 minutes;
3. Fmoc group removed using 50% piperidine solution in NMP for 5 minutes, resin washed, and sequence repeated 3 to 4 times;
4. Fmoc-amino acid activated with 1 mM of 0.5M HATU in DMF;
5. Activated Fmoc-amino acid added to the reaction vessel followed by addition of 1 mM of 2M diisopropylamine in NMP solution;
6. Fmoc-amino acid coupled for 20 minutes;
7. Resin washed and Fmoc-group removed using 50% piperidine in NMP.

The following protected amino acids were sequentially coupled to the resin using the above protocol:

| Amino acid | Coupling time |
|---|---|
| 1. Fmoc-Arg(Pmc) | 20 minutes |
| 2. Fmoc-Ile | 20 minutes |
| 3. Fmoc-NMeNva | 20 minutes |
| 4. Fmoc-Thr(t-Bu) | 20 minutes |
| 5. Fmoc-D-Ile | 20 minutes |
| 6. Fmoc-Val | 20 minutes |
| 7. Fmoc-Gly | 20 minutes |
| 8. Fmoc-Sar | 20 minutes |
| 9. acetic acid | 20 minutes |

Upon completion of the synthesis the resin-bound peptide was washed with methanol three times and dried in vacuo, then treated with a (95:5) TFA/water solution (3 mL) at room temperature overnight. The resin was filtered and washed 3 times with methanol. The filtrates and the washes were combined and concentrated in vacua. The residue was treated with diethyl ether and the precipitate was filtered to provide the crude peptide as an amorphous powder. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-NMeNva-Ile-Arg-ProNH-ethyl as a trifluoroacetate salt; $R_t$=4.259 minutes (using a C-18 column and a solvent system increasing in gradient from 20% to 95% acetonitrile/water containing 10 mM ammonium acetate over a period of 10 minutes); MS (ESI) m/e 1008 (M+H); Amino Acid Anal.: 1.14 Pro; 1.70 Arg; 1.96 Ile; 0.47 Thr; 0.97 Val; 0.90 Gly; 0.98 Sar.

EXAMPLE 2

N-Ac-Sar-Gly-Val-D-Ile-Thr-Nva-NMeIle-Arg-ProNH-ethyl

The desired product was prepared by substituting Fmoc-Nva for Fmoc-NMeNva and Fmoc-NMeIle for Fmoc-Ile in Example 1. Upon completion of the synthesis, cleavage of the peptide from the resin, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-Nva-NMeIle-Arg-ProNH-ethyl as a trifluoroacetate salt; $R_t$=4.416 minutes (using a C-18 column and a solvent system increasing in gradient from 20% to 95% acetonitrile/water containing 10 mM ammonium acetate over a period of 10 minutes); MS (ESI) m/e 1008 (M+H); Amino Acid Anal.: 1.05 Pro; 1.26 Arg; 1.0 Ile; 0.54 Thr; 1.29 Nva; 1.02; Val; 0.94 Gly; 1.01 Sar.

EXAMPLE 3

N-Ac-Sar-Gly-Val-D-lie-Thr-NMeAla-Ile-Arg-ProNH-ethyl

The desired product was prepared by substituting Fmoc-NMeAla for Fmoc-NMeNva in Example 1. Upon completion of the synthesis, cleavage of the peptide from the resin, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-NMeAla-Ile-Arg-ProNH-ethyl as a trifluoroacetate salt; $R_t$=2.84 minutes (using a C-18 column and a solvent system increasing in gradient from 20% to 95% acetonitrile/water containing 10 mM ammonium acetate over a period of 10 minutes); MS (ESI) m/e 980 (M+H); Amino Acid Anal.: 0.99 Pro; 1.54 Arg; 2.10 Ile; 0.50 Thr; 0.95 Val; 0.96 Gly; 0.98 Sar.

EXAMPLE 4

N-Ac-Sar-Gly-Val-D-Ile-Thr-NMeVal-Ile-Arg-ProNH-ethyl

The desired product was prepared by substituting Fmoc-NMeVal for Fmoc-NMeNva in Example 1. Upon completion of the synthesis, cleavage of the peptide from the resin, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-NMeVal-Ile-Arg-ProNH-ethyl as a trifluoroacetate salt; $R_t$=3.11 minutes (using a C-18 column and a solvent system increasing in gradient from 20% to 95% acetonitrile/water containing 10 mM ammonium acetate over a period of 10 minutes); MS (ESI) m/e 1008 (M+H); Amino Acid Anal.: 1.03 Pro; 1.47 Arg; 2.06 Ile; 0.49 Thr; 0.96 Val; 1.01 Gly; 0.99 Sar.

EXAMPLE 5

N-Ac-Sar-Gly-Val-D-Ile-Thr-Nva-Ile-Arg-NMeAlaNH-ethyl

The desired product was prepared by substituting Fmoc-Nva for Fmoc-NMeNva and Fmoc-NMeAla for Fmoc-Pro in Example 1. Upon completion of the synthesis, cleavage of the peptide from the resin, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-Nva-Ile-Arg-NMeAlaNH-ethyl as a trifluoroacetate salt; $R_t$=2.84 minutes (using a C-18 column and a solvent system increasing in gradient from 20% to 95% acetonitrile/water containing 10 mM ammonium acetate over a period of 10 minutes); MS (ESI) m/e 982 (M+H); Amino Acid Anal.: 1.46 Arg; 2.02 Ile; 1.04 Nva; 0.47 Thr; 0.98 Val; 0.96 Gly; 1.03 Sar.

EXAMPLE 6

N-Ac-Sar-Gly-Val-D-Ile-Thr-Nva-Ile-Arg-SarNH-ethyl

The desired product was prepared by substituting Fmoc-Nva for Fmoc-NMeNva and Fmoc-Sar for Fmoc-Pro in Example 1. Upon completion of the synthesis, cleavage of the peptide from the resin, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-Nva-Ile-Arg-SarNH-ethyl as a trifluoroacetate salt; $R_t$=2.92 minutes (using a C-18 column and a solvent system increasing in gradient from 20% to 95% acetonitrile/water containing 10 mM ammonium acetate over a period of 10 minutes); MS (ESI) m/e 968 (M+H); Amino Acid Anal.: 1.49 Arg; 2.07 Ile; 1.05 Nva; 0.55 Thr; 0.98 Val; 0.96 Gly; 1.96 Sar.

EXAMPLE 7

N-Succinyl-Sar-Gly-Val-D-Ile-Thr-NMeNva-Ile-Arg-ProNH-ethyl

The desired product was prepared by the procedure described in Example 1 with the following modification: coupling with acetic acid at the end of the synthesis was replaced with treatment of the peptide resin overnight with a 10-fold excess of succinic anhydride/pyridine in NMP. Upon completion of the synthesis, washing of the resin-bound peptide, cleavage of the peptide from the resin, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Succinyl-Sar-Gly-Val-D-Ile-Thr-NMeNva-Ile-Arg-ProNH-ethyl as a trifluoroacetate salt; $R_t$=2.61 minutes (using a C-18 column and a solvent system increasing in gradient from 20% to 95% acetonitrile/water containing 10 mM ammonium acetate over a period of 10 minutes); MS (ESI) m/e 1066 (M+H); Amino Acid Anal.: 1.59 Arg; 2.23 Ile; 0.50 Thr; 1.01 Val; 1.00 Gly; 1.02 Sar; 0.99 Pro.

EXAMPLE 8

N-Succinyl-Sar-Gly-Val-D-Leu-Thr-NMeNva-Ile-Arg-ProNH-ethyl

The desired product was prepared by substituting Fmoc-D-Leu for Fmoc-D-Ile in Example 7. Upon completion of the synthesis, washing of the resin-bound peptide, cleavage of the peptide from the resin, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-succinyl-Sar-Gly-Val-D-Leu-Thr-NMeNva-Ile-Arg-ProNH-ethyl as a trifluoroacetate salt; $R_t$=2.67 minutes (using a C-18 column and a solvent system increasing in gradient from 20% to 95% acetonitrile/water containing 10 mM ammonium acetate over a period of 10 minutes); MS (ESI) m/e 1066 (M+H); Amino Acid Anal.: 1.61 Arg; 1.01 Ile; 1.10 Leu; 0.45 Thr; 0.95 Val; 0.95 Gly; 1.01 Sar, 0.93 Pro.

EXAMPLE 9

N-Ac-Sar-NMeAla-Val-D-Ile-Thr-Nva-Ile-Arg-ProNH-ethyl

The desired product was prepared by substituting Fmoc-NMeAla for Fmoc-Gly and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-NMeAla-Val-D-Ile-Thr-Nva-Ile-Arg-ProNH-ethyl as a trifluoroacetate salt; $R_t$=3.43 minutes (using a C-18 column and a solvent system increasing in gradient from 20% to 95% acetonitrile/water containing 10 mM ammonium acetate over a period of 10 minutes); MS (ESI) m/e 1022 (M+H).

EXAMPLE 10

N-Ac-Sar-Gly-Val-D-Ile-Thr-Nva-Ile-NMeArg-ProNH-ethyl

The desired product was prepared by substituting Fmoc-Nva for Fmoc-NMeNva and Fmoc-NMeArg(Mtr) for Fmoc-Arg(Pmc) in Example 1. Upon completion of the synthesis, cleavage of the peptide from the resin, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-Nva-Ile-NMeArg-ProNH-ethyl as a trifluoroacetate salt; $R_t$=3.43 minutes (using a C-18 column and a solvent system increasing in gradient from 20% to 95% acetonitrile/water containing 10 mM ammonium acetate over a period of 10 minutes); MS (ESI) m/e 1008 (M+H).

EXAMPLE 11

N-Ac-S ar-Gly-NMeVal-D-Ile-Thr-Nva-Ile-Arg-ProNH-ethyl

The desired product was prepared by substituting Fmoc-NMeVal for Fmoc-Val and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-NMeVal-D-Ile-Thr-Nva-Ile-Arg-ProNH-ethyl as a trifluoroacetate salt; $R_t$=3.42 minutes (using a C-18 column and a solvent system increasing in gradient from 20% to 95% acetonitrile/water containing 10 mM ammonium acetate over a period of 10 minutes); MS (ESI) m/e 1008 (M+H).

EXAMPLE 12

N-Ac-Sar-Glv-NMeIle-D-Ile-Thr-Nva-Ile-Arg-ProNH-ethyl

The desired product was prepared by substituting Fmoc-NMeIle for Fmoc-Val and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-NMeIle-D-Ile-Thr-Nva-Ile-Arg-ProNH-ethyl as a trifluoroacetate salt; $R_t$=3.83 minutes (using a C-18 column and a solvent system increasing in gradient from 20% to 95% acetonitrile/water containing 10 mM ammonium acetate over a period of 10 minutes); MS (ESI) m/e 1022 (M+H).

EXAMPLE 13

N-Ac-S ar-Gly-NMePhe-D-Ile-Thr-Nva-Ile-Arg-ProNH-ethyl

The desired product was prepared by substituting Fmoc-NMePheAla for Fmoc-Val and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-NMePhe-D-Ile-Thr-Nva-Ile-Arg-ProNH-ethyl as a trifluoroacetate salt; $R_t$=4.00 minutes (using a C-18 column and a solvent system increasing in gradient from 20% to 95% acetonitrile/water containing 10 mM ammonium acetate over a period of 10 minutes); MS (ESI) m/e 1056 (M+H).

EXAMPLE 14

N-Ac-Sar-Glv-NMeNva-D-Ile-Thr-Nva-Ile-Arg-ProNH-ethyl

The desired product was prepared by substituting Fmoc-NMeNva for Fmoc-Val and Fmoc-Nva for Fmoc-NMeNva in Example 1. Upon completion of the synthesis, cleavage of the resin-bound peptide from the resin, removal of the protecting groups, and precipitation with diethyl ether, the crude peptide was obtained. This was purified by preparative HPLC using a C-18 column with a solvent system increasing in gradient from 5% to 100% acetonitrile/water containing 0.01% TFA over a period of 50 minutes. The pure fractions were lyophilized to provide N-Ac-Sar-Gly-NMeNva-D-Ile-Thr-Nva-Ile-Arg-ProNH-ethyl as a trifluoroacetate salt; $R_t$=3.55 minutes (using a C-18 column and a solvent system increasing in gradient from 20% to 95% acetonitrile/water containing 10 mM ammonium acetate over a period of 10 minutes); MS (ESI) m/e 1008 (M+H).

EXAMPLE 17

N-Ac-Sar-Glv-NMeAla-D-Ile-Thr-Nva-Ile-Arg-ProNH-ethyl

The procedure described in Example 1 was used substituting Fmoc-NMeAla for Fmoc-Val and Fmoc-Nva for Fmoc-NMeNva. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-NMeAla-D-Ile-Thr-Nva-Ile-Arg-ProNH-ethyl as a trifluoroacetate salt; MS (ESI) m/e 978 (M+H).

EXAMPLE 18

N-MePro-Sar-Gly-Val-D-Ile-Thr-Nva-Ile-Arg-ProNH-ethyl

The desired product was prepared by substituting NMe-Pro for acetic acid and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-MePro-Sar-Gly-Val-D-Ile-Thr-Nva-Ile-Arg-ProNH-ethyl as a trifluoroacetate salt; MS (ESI) m/e 1063 (M+H).

EXAMPLE 21

N-Ac-Sar-Glv-Val-D-Ile-NMeThr(Bzl)-Nva-Ile-ArR-ProNH-ethyl

The desired product was prepared by substituting Fmoc-NMeThr(Bzl) for Fmoc-Thr(t-Bu) and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-Ile-NMeThr(Bzl)-Nva-Ile-Arg-ProNH-ethyl as a trifluoroacetate salt; MS (ESI) m/e 1084 (M+H).

EXAMPLE 22

N-Ac-Sar-Gly-Val-D-Ile-Thr-Sar-Ile-Arg-ProNH-ethyl

The desired product was prepared by substituting Fmoc-Sar for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-Sar-Ile-Arg-ProNH-ethyl as a trifluoroacetate salt; $R_t$=2.68 minutes (using a C-18 column and a solvent system increasing in gradient from 20% to 95% acetonitrile/water containing 10 mM ammonium acetate over a period of 10 minutes); MS (ESI) m/e 966 (M+H); Amino Acid Anal.: 1.07 Pro; 1.21 Arg; 2.11 Ile; 0.47 Thr, 1.01; Val; 0.97 Gly; 2.07 Sar.

EXAMPLE 23

N-Ac-Sar-Gly-Val-D-Leu-Sar-Nva-Ie-Arg-ProNH-ethyl

The desired product was prepared by substituting Fmoc-D-Leu for Fmoc-D-Ile, Fmoc-Sar for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-Leu-Sar-Nva-Ile-Arg-ProNH-ethyl as a trifluoroacetate salt; MS (ESI) m/e 964 (M+H).

EXAMPLE 24

N-Ac-Sar-Gly-NMeLeu-D-Ile-Thr-Nva-Ile-Arg-ProNH-ethyl

The desired product was prepared by substituting Fmoc-NMeLeu for Fmoc-Val and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-NMeLeu-D-Ile-Thr-Nva-Ile-Arg-ProNH-ethyl as a trifluoroacetate salt; MS (ESI) m/e 1022 (M+H).

EXAMPLE 25

N-Ac-Sar-Gly-Val-D-Ile-Thr-NMeLeu-Ile-Arg-ProNH-ethyl

The desired product was prepared by substituting Fmoc-NMeLeu for Fmoc-NMeva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-NMeLeu-Ile-Arg-ProNH-ethyl as a trifluoroacetate salt; MS (ESI) m/e 1022 (M+H).

EXAMPLE 26

N-Ac-Sar-Gly-Val-D-alloIle-Thr-NMeNva-Ile-Arg-ProNH-ethyl

The desired product was prepared by substituting Fmoc-D-alloIle for Fmoc-D-Ile in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-alloIle-Thr-NMeNva-Ile-Arg-ProNH-ethylas a trifluoroacetate salt; MS (ESI) m/e 1008 (M+H).

EXAMPLE 27

N-Ac-Sar-Gly-Val-D-alloIle-Thr-NMeVal-Ile-Arg-ProNH-ethyl

The desired product can be prepared by substituting Fmoc-D-alloIle for Fmoc-D-Ile and Fmoc-NMeVal for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-alloIle-Thr-NMeVal-Ile-Arg-ProNH-ethyl as a trifluoroacetate salt.

EXAMPLE 28

N-Ac-Sar-Glv-Val-D-Ile-Thr-NMeNva-Ile-Arg-Pro-D-AlaNH$_2$

The desired product was prepared using the procedure in Example 1 with the following modifications: Fmoc-D-Ala-Sieber amide resin was substituted for Fmoc-Pro-Sieber ethylamide resin, and a coupling with Fmoc-Pro prior was added prior to the coupling with Fmoc-Arg(Pmc). Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-NMeNva-Ile-Arg-Pro-D-AlaNH$_2$ as a trifluoroacetate salt; MS (ESI) m/e 1051 (M+H).

EXAMPLE 29

N-Ac-Sar-Gly-Val-D-Ile-Thr-NMeVal-Ile-Arg-Pro-D-AlaNH$_2$

The desired product was prepared by substituting Fmoc-NMeVal for Fmoc-NMeNva in Example 28. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-NMeVal-Ile-Arg-Pro-D-AlaNH$_2$ as a trifluoroacetate salt; $R_t$=3.54 minutes (using a C-18 column and a solvent system increasing in gradien from 20% to 95% acetonitrile/water containing 10 mM ammonium acetate over a period of 10 minutes); MS (ESI) m/e 1051 (M+H); Amino Acid Anal.: 1.00 Pro; 1.13 Arg; 2.07 Ile; 0.53 Thr; 1.05 Ala; 1.03 Val; 1.05 Gly; 1.03 Sar.

EXAMPLE 30

N-Ac-Sar-Gly-Val-D-Ile-NMeThr-Nva-Ile-Arg-ProNH-ethyl

The desired product can be prepared by substituting Fmoc-NMeThr(r-Bu) for Fmoc-Thr(t-Bu) and Fmoc-Nva for Fmoc-NMeNva in Example 1. Upon completion of the synthesis, cleavage of the resin-bound peptide, removal of the protecting groups, and precipitation with diethyl ether, the crude peptide can be obtained. This can be purified purified by preparative HPLC using a C-18 column and a solvent system increasing in gradient from 5% to 100% acetonitrile/water containing 0.01% TFA over a period of 50 minutes. The pure fractions can then be lyophilized to provide N-Ac-Sar-Gly-Val-D-Ile-NMeThr-Nva-Ile-Arg-ProNH-ethyl as a trifluoroacetate salt.

EXAMPLE 31

N-Ac-Sar-Gly-Val-D-Ile-NMeSer-Nva-Ile-Arg-ProNH-ethyl

The desired product was prepared by substituting Fmoc-NMeSer(t-Bu) for Fmoc-Thr(t-Bu) and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-Ile-NMeSer-Nva-Ile-Arg-ProNH-ethyl as a trifluoroacetate salt; $R_t$=3.01 minutes (using a C-18 column and a solvent mixture increasing in gradient from 10% to 95% acetonitrile/water containing 0.01% TFA over a period of 10 minutes); MS (ESI) m/e 994.7 (M+H).

EXAMPLE 32

N-Ac-Sar-Gly-Val-D-Leu-NMeSer-Nva-Ile-Arg-ProNH-ethyl

The desired product can be prepared by substituting Fmoc-D-Leu for Fmoc-D-Ile, Fmoc-NMeSer(t-Bu) for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-Leu-NMeSer-Nva-Ile-Arg-ProNH-ethyl as a trifluoroacetate salt.

EXAMPLE 33

N-Ac-Sar-Gly-Val-D-Leu-Ser-NMeNva-Ile-Arg-ProNH-ethyl

The desired product can be prepared by substituting Fmoc-D-Leu for Fmoc-D-Ile and Fmoc-Ser(t-Bu) for Fmoc-Thr(t-Bu) in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-Leu-Ser-NMeNva-Ile-Arg-ProNH-ethyl as a trifluoroacetate salt.

EXAMPLE 34

N-Ac-Sar-Glv-Val-D-alloIle-Ser-NMeSer-Ile-Arg-ProNH-ethyl

The desired product was prepared by substituting Fmoc-D-alloIle for Fmoc-D-Ile, Fmoc-Ser(t-Bu) for Fmoc-Thr(t-Bu), and Fmoc-NMeSer(t-Bu) for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-alloIle-Ser-NMeSer-Ile-Arg-ProNH-ethyl as a trifluoroacetate salt; $R_t$=3.21 minutes (using a C-18 column and a solvent system increasing in gradient from 20% to 95% acetonitrile/water containing 10 mM ammonium acetate over a period of 10 minutes); MS (ESI) m/e 982 (M+H); Amino Acid Anal.: 1.02 Pro; 1.32 Arg; 2.12 Ile; 0.31 Ser; 1.01 Val; 1.03 Gly; 0.94 Sar.

EXAMPLE 35

N-Ac-Sar-Glv-Val-D-alloIle-Thr-NMeSer-Ile-Arg-ProNH-ethyl

The desired product was prepared by substituting Fmoc-D-alloIle for Fmoc-D-Ile and Fmoc-NMeSer(t-Bu) for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-alloIle-Thr-NMeSer-Ile-Arg-ProNH-ethyl as a trifluoroacetate salt; $R_t$=2.82 minutes (using a C-18 column and a solvent mixture increasing in gradient from 10% to 95% acetonitrile/water containing 0.01% TFA over a period of 10 minutes); MS (ESI) m/e 996.7 (M+H).

EXAMPLE 36

N-Ac-Sar-Gly-Val-D-Ile-Thr-NMeSer-Ile-Arg-ProNH-ethyl

The desired product was prepared by substituting Fmoc-NMeSer(t-Bu) for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide N-Ac-Sar-Gly-Val-D-Ile-Thr-NMeSer-Ile-Arg-ProNH-ethylas a trifluoroacetate salt; $R_t$=2.77 minutes (using a C-18 column and a solvent system increasing in gradient from 10% to 95% acetonitrile/water containing 0.01% TFA over a period of 10 minutes); MS (ESI) m/e 996.6 (M+H).

EXAMPLE 37

N-Ac-Sar-Gly-Val-D-alloIle-Thr-NMeSer-Ile-Arg-Pro-D-AlaNH$_2$

The desired product can be prepared by substituting Fmoc-D-alloIle for Fmoc-DIle and Fmoc-NMeSer(t-Bu) for Fmoc-NMeNva in Example 28. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-alloIle-Thr-NMeSer-Ile-Arg-Pro-D-AlaNH$_2$ as a trifluoroacetate salt.

EXAMPLE 38

N-Ac-Sar-Gly-Phe-D-Ile-Thr-NMeVal-Ile-Arg-Pro-D-AlaNH$_2$

The desired product can be prepared by substituting Fmoc-PheAla for Fmoc-Val and Fmoc-NMeVal for Fmoc-Nva in Example 28. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Phe-D-Ile-Thr-NMeVal-Ile-Arg-Pro-D-AlaNH$_2$ as a trifluoroacetate salt.

EXAMPLE 39

N-Ac-Sar-Gly-Val-D-alloIle-Tyr-NMeNva-Ile-Arg-ProNH-ethyl

The desired product can be prepared by substituting Fmoc-D-alloIle for Fmoc-DIle and Fmoc-Tyr(t-Bu) for Fmoc-Thr(t-Bu) in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-alloIle-Tyr-NMeNva-Ile-Arg-ProNH-ethyl as a trifluoroacetate salt.

EXAMPLE 40

N-Ac-Sar-Gly-Val-D-alloIle-Tyr-NMeVal-Ile-Arg-ProNH-ethyl

The desired product can be prepared by substituting Fmoc-D-alloIle for Fmoc-D-Ile, Fmoc-Tyr(t-Bu) for Fmoc-Thr(t-Bu), and Fmoc-NMeVal for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-alloIle-Tyr-NMeVal-Ile-Arg-ProNH-ethyl as a trifluoroacetate salt.

EXAMPLE 41

N-Ac-Sar-Gly-Gln-D-Ile-Thr-NMeNva-Ile-Arg-Pro-D-AlaNH$_2$

The desired product can be prepared by substituting Fmoc-Gln(Trt) for Fmoc-Val in Example 28. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Gln-D-Ile-Thr-NMeNva-Ile-Arg-Pro-D-AlaNH$_2$ as a trifluoroacetate salt.

EXAMPLE 43

N-Ac-Sar-Gly-Val-D-alloIle-NMeThr-Nva-Ile-Arg-ProNH-ethyl

The desired product can be prepared by substituting Fmoc-D-alloIle for Fmoc-D-Ile, Fmoc-NMeThr(t-Bu) for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-alloIle-NMeThr-Nva-Ile-Arg-ProNH-ethyl as trifluoroacetate salt.

EXAMPLE 44

N-Ac-Sar-Gly-Val-D-Ile-Thr-NMeSer-Ile-Arg-Pro-D-AlaNH$_2$

The desired product can be prepared by Fmoc-NMeSer(t-Bu) for Fmoc-NMeNva in Example 28. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-Ile-Thr-NMeSer-Ile-Arg-Pro-D-AlaNH$_2$ as trifluoroacetate salt.

EXAMPLE 45

N-Ac-Sar-Gly-NMeVal-D-Ile-Thr-Nva-Ile-Arg-Pro-D-AlaNH$_2$

The desired product can be prepared by substituting Fmoc-NMeVal for Fmoc-Val and Fmoc-Nva for Fmoc-NMeNva in Example 28. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-NMeVal-D-Ile-Thr-Nva-Ile-Arg-Pro-D-AlaNH$_2$ as trifluoroacetate salt.

EXAMPLE 46

N-Ac-Sar-Gly-NMeVal-D-alloIle-Thr-Nva-Ile-Arg-ProNH-ethyl

The desired product can be prepared by substituting Fmoc-NMeVal for Fmoc-Val, Fmoc-D-alloIle for Fmoc-D-Ile, and Fmoc-Nva for Fmoc NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-NMeVal-D-alloIle-Thr-Nva-Ile-Arg-ProNH-ethyl as trifluoroacetate salt.

EXAMPLE 47

N-Ac-Sar-Gly-Val-D-HpheAla-Thr-NMeNva-Ile-Arg-ProNH-ethyl

The desired product can be prepared by substituting Fmoc-D-HpheAla for Fmoc-D-Ile in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-HpheAla-Thr-NMeNva-Ile-Arg-ProNH-ethyl as trifluoroacetate salt.

EXAMPLE 48

N-Ac-Sar-Gly-Val-D-HpheAla-Thr-NMeVal-Ile-Arg-ProNH-ethyl

The desired product can be prepared by substituting Fmoc-D-HpheAla for Fmoc-D-Ile and Fmoc-NMeVal for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-HpheAla-Thr-NMeVal-Ile-Arg-ProNH-ethyl as trifluoroacetate salt.

EXAMPLE 49

N-Ac-Sar-Gly-Val-D-Pen(SMe)-Thr-NMeNva-Ile-Arg-ProNH-ethyl

The desired product can be prepared by substituting Fmoc-D-Pen(SMe) for Fmoc-D-Ile in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-Pen(SMe)-Thr-NMeNva-Ile-Arg-ProNH-ethyl as trifluoroacetate salt.

EXAMPLE 50

N-Ac-Sar-Gly-Val-D-Pen(SMe)-Thr-NMeVal-Ile-Arg-ProNH-ethyl

The desired product can be prepared by substituting Fmoc-D-Pen(SMe) for Fmoc-D-Ile and Fmoc-NMeVal for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-Pen(SMe)-Thr-NMeVal-Ile-Arg-ProNH-ethyl as trifluoroacetate salt.

EXAMPLE 51

N-Ac-Sar-Gly-Val-D-alloIle-NMeSer-Ser-Ile-Arg-ProNH-ethyl

The desired product can be prepared by substituting Fmoc-D-alloIle for Fmoc-D-Ile, Fmoc-NMeSer(t-Bu) for Fmoc-Thr(t-Bu), and Fmoc-Ser(t-Bu) for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide N-Ac-Sar-Gly-Val-D-alloIle-NMeSer-Ser-Ile-Arg-ProNH-ethyl as trifluoroacetate salt; $R_t$=3.21 minutes (using a C-18 column and a solvent system increasing in gradient from 20% to 95% acetonitrile/water containing 10 mM ammonium acetate over a period of 10 minutes); MS (ESI) m/e 982 (M+H); Amino Acid Anal.: 1.05 Pro; 0.93 Arg; 0.35 Ser; 2.01 Ile; 0.96 Val; 1.01 Gly; 0.99 Sar.

EXAMPLE 54

NAc-Sar-Gly-Val-NMe-D-Leu-Thr-Nva-Ile-Arg-ProNH-ethyl

The desired product was prepared by substituting Fmoc-NMe-D-Leu for Fmoc-D-Ile and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 min. The pure fractions were lyophilized to provide NAc-Sar-Gly-Val-NMe-D-Leu-Thr-Nva-Ile-Arg-ProNH-ethyl as trifluoroacetate salt, $R_t$=3.87 minutes (using a C-18 column and a solvent system increasing in gradient from 20% to 95% acetonitrile/water containing 10 mM ammonium acetate over a period of 10 min); MS (ESI) m/e 1008 (M+H); Amino Acid Anal.: 0.98 Pro; 0.99 Arg; 1.04 Ile; 0.99 Nva; 0.55 Thr; 1.06 Val; 0.98 Gly; 1.00 Sar.

EXAMPLE 55

NAc-Sar-Gly-Val-D-Ile-Thr-Nva-Ile-Arg-NMeNvaN-ethyl

The desired product was prepared by substituting Fmoc-Nva for Fmoc-NMeNva and Fmoc-NMeNva-Sieber ethylamide resin for Fmoc-Pro-Sieber ethylamide resin in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 min. The pure fractions were lyophilized to provide NAc-Sar-Gly-Val-D-Ile-Thr-Nva-Ile-Arg-NMeNvaNH-ethyl as trifluoroacetate salt; $R_t$=4.21 minutes (using a C-18 column and a solvent system increasing in gradient from 20% to 95% acetonitrile/water containing 10 mM ammonium acetate over a period of 10 minutes); MS (ESI) m/e 1010 (M+H); Amino Acid Anal.: 0.99 Arg; 2.04 Ile; 1.03 Nva; 0.55 Thr; 1.0 Val; 0.97 Gly; 0.98 Sar.

EXAMPLE 56

NAc-Sar-Gly-Val-NMe-D-Leu-Ser-Nva-Ile-Arg-ProNH-ethyl

The desired product was prepared by substituting. Fmoc-NMe-D-Leu for Fmoc-D-Ile, Fmoc-Ser(t-Bu) for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-NMe-D-Leu-Ser-Nva-Ile-Arg-ProNH-ethyl as trifluoroacetate salt; $R_t$=3.36 minutes (using a C-18 column and a solvent system increasing in gradient from 10% to 95% acetonitrile/water containing 0.01% TFA over a period of 10 minutes); MS (ESI) m/e 994.7 (M+H).

EXAMPLE 57

NAc-Sar-Gly-Asn-NMe-D-Leu-Ser-Nva-Ile-Arg-ProNH-ethyl

The desired product was prepared by substituting Fmoc-Asn(Trt) for Fmoc-Val, Fmoc-NMe-D-Leu for Fmoc-D-Ile, Fmoc-Ser(t-Bu) for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Asn-NMe-D-Leu-Ser-Nva-Ile-Arg-ProNH-ethyl as trifluoroacetate salt; $R_t$=2.39 minutes (using a C-18 column and a solvent system increasing in gradient from 10% to 95% acetonitrile/water containing 0.01% TFA over a period of 10 minutes); MS (ESI) m/e 1009.7 (M+H).

EXAMPLE 58

NAc-Sar-Gly-NMeNva-D-alloIle-Thr-Nva-Ile-Arg-ProNH-ethyl

The desired product was prepared by substituting Fmoc-NMeNva for Fmoc-Val, Fmoc-D-alloIle for Fmoc-D-Ile, and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-NMeNva-D-alloIle-Thr-Nva-Ile-Arg-ProNH-ethyl as trifluoroacetate salt; $R_t$=3.31 minutes (using a C-18 column and a solvent system increasing in gradient from 10% to 95% acetonitrile/water containing 0.01% TFA over a period of 10 minutes); MS (ESI) m/e 1008.7 (M+H); Amino acid Anal.: 0.99 Pro; 0.99 Arg; 0.91 Nva; 0.49 Thr; 2.14 Ile; 0.97 Gly; 1.00 Sar.

EXAMPLE 59

NAc-Sar-Gly-Asn-D-Leu-NMeSer-Nva-Ile-Arg-ProNH-ethyl

The desired product was prepared by substituting Fmoc-Asn(Trt) for Fmoc-Val, Fmoc-D-Leu for Fmoc-D-Ile, Fmoc-NMeSer(t-Bu) for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Asn-D-Leu-NMeSer-Nva-Ile-Arg-ProNH-ethyl as trifluoroacetate salt; $R_t$=2.28 minutes (using a C-18 column and a solvent system increasing in gradient from 10% to 95% acetonitrile/water containing 0.01% TFA over a period of 10 minutes); MS (ESI) m/e 1009.7 (M+H).

EXAMPLE 60

NAc-Sar-Gly-NMePhe-D-Ile-Thr-Nva-Ile-Arg-Pro-D-AlaNH$_2$

The desired product was prepared by substituting Fmoc-NMePheAla for Fmoc-Val and Fmoc-Nva for Fmoc-NMeNva in Example 28. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-NMePhe-D-Ile-Thr-Nva-Ile-Arg-Pro-D-AlaNH$_2$ as trifluoroacetate salt; $R_t$=3.45 minutes (using a C-18 column and a solvent system increasing in gradient from 10% to 95% acetonitrile/water containing 0.01% TFA over a period of 10 minutes); MS (ESI) m/e 1099.7 (M+H).

EXAMPLE 61

NAc-Sar-Gly-Val-D-alloIle-NMeSer-Nva-Ile-Arg-ProNH-ethyl

The desired product can be prepared by substituting Fmoc-D-alloIle for Fmoc-D-Ile, Fmoc-NMeSer(t-Bu) for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide NAc-Sar-Gly-Val-D-alloIle-NMeSer-Nva-Ile-Arg-ProNH-ethyl as trifluoroacetate salt.

EXAMPLE 80

NAc-Sar-Gly-Val-D-Ile-Thr-NMeNle-Ile-Arg-ProNH-ethyl

The desired product was prepared by substituting Fmoc-NMeNle for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-Ile-Thr-NMeNle-Ile-Arg-ProNH-ethyl as trifluoroacetate salt; $R_t$=3.45 minutes (using a C-18 column and a solvent system increasing in gradient from 10% to 95% acetonitrile/water containing 0.01% TFA over a period of 10 minutes); MS (ESI) m/e 1022 (M+H); Amino Acid Anal.: 1.03 Pro; 1.09 Arg; 0.45 Thr; 1.81 Ile; 1.07 Val; 1.01 Gly; 1.04 Sar.

EXAMPLE 81

NAc-Sar-Gly-Val-D-Ile-Sar-Nva-Ile-Arg-ProNH-ethyl

The desired product was prepared by substituting Fmoc-Sar for Fmoc-Thr(t-Bu) and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-Ile-Sar-Nva-Ile-Arg-ProNH-ethyl as trifluoroacetate salt; $R_t$=3.16 minutes (using a C-18 column and a solvent system increasing in gradient from 10% to 95% acetonitrile/water containing 0.01% TFA over a period of 10 minutes); MS (ESI) m/e 964.7 (M+H); Amino Acid Anal.: 1.01 Pro; 1.00 Arg; 0.92 Nva; 2.04 Ile; 1.04 Val; 0.99 Gly; 2.01 Sar.

EXAMPLE 82

NAc-Sar-Gly-Val-D-alloIle-Sar-Nva-Ile-Arg-ProNH-ethyl

The desired product was prepared by substituting Fmoc-D-alloIle for Fmoc-D-Ile, Fmoc-Sar for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-alloIle-Sar-Nva-Ile-Arg-ProNH-ethyl as trifluoroacetate salt; $R_t$=3.15 minutes (using a C-18 column and a solvent system increasing in gradient from 10% to 95% acetonitrile/water containing 0.01% TFA over a period of 10 minutes); MS (ESI) m/e 964.7 (M+H); Amino Acid Anal.: 1.00 Pro; 0.99 Arg; 0.90 Nva; 2.11 Ile; 1.03 Val; 0.96 Gly; 1.96 Sar.

EXAMPLE 83

NAc-Sar-Gly-Val-D-Ile-Thr-Nva-NMeAla-Arg-ProNH-ethyl

The desired product was prepared by substituting Fmoc-Nva for Fmoc-NMeNva and Fmoc-NMeAla for Fmoc-Ile in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-Ile-Thr-Nva-NMeAla-Arg-ProNH-ethyl as trifluoroacetate salt; $R_t$=2.86 minutes (using a C-18 column and a solvent system increasing in gradient from 10% to 95% acetonitrile/water containing 0.01% TFA over a period of 10 minutes); MS (ESI) m/e 966.7 (M+H); Amino Acid Anal.: 0.97 Pro; 0.98 Arg; 0.97 Nva; 0.51 Thr; 1.09 Ile; 1.02 Val; 0.96 Gly; 1.10 Sar.

EXAMPLE 84

NAc-Sar-Gly-Val-D-Ile-NMeAsp-Nva-Ile-Arg-ProNH-ethyl

The desired product was prepared by substituting Fmoc-NMeAsp(t-Bu) for Fmoc-Thr(t-Bu) and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-Ile-NMeAsp-Nva-Ile-Arg-ProNH-ethyl as trifluoroacetate salt; $R_t$=2.89 minutes (using a C-18 column and a solvent system increasing in gradient from 10% to 95% acetonitrile/water containing 0.01% TFA over a period of 10 minutes); MS (ESI) m/e 1022.7 (M+H); Amino Acid Anal.: 1.02 Pro; 1.02 Arg; 0.92 Nva; 2.01 Ile; 1.04 Val; 1.00 Gly; 0.98 Sar.

EXAMPLE 85

NAc-Sar-Gly-Val-D-Ile-Thr-NMe-D-Leu-Ile-Arg-ProNH-ethyl

The desired product was prepared by substituting Fmoc-NMe-D-Leu for NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-Ile-Thr-NMe-D-Leu-Ile-Arg-ProNH-ethyl as trifluoroacetate salt; $R_t$=3.58 minutes (using a C-18 column and a solvent system increasing in gradient from 10% to 95% acetonitrile/water containing 0.01% TFA over a period of 10 minutes); MS (ESI) m/e 1022.8 (M+H); Amino Acid Anal.: 1.04 Pro; 1.03 Arg; 0.47 Thr; 1.87 Ile; 1.06 Val; 1.01 Gly; 1.05 Sar.

EXAMPLE 86

NAc-Sar-Gly-Val-D-Ile-NMeGlu-Nva-Ile-Arg-ProNH-ethyl

The desired product was prepared by substituting Fmoc-NMeGlu(t-Bu) for Fmoc-Thr(t-Bu) and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a solvent system increasing in gradient from 5% to 100% acetonitrile/water containing 0.01% TFA over a period of 50 minutes. The pure fractions were lyophilized to provide NAc-Sar-Gly-Val-D-Ile-NMeGlu-Nva-Ile-Arg-ProNH-ethyl as trifluoroacetate salt; $R_t$=3.12 minutes (using a C-18 column and a solvent system increasing in gradient from 10% to 95% acetonitrile/water containing 0.01% TFA over a period of 10 minutes); MS (ESI) m/e 1036.7 (M+H); Amino Acid Anal.: 1.01 Pro; 1.0 Arg; 0.93 Nva; 2.04 Ile; 1.04 Val; 0.98 Gly; 1.0 Sar.

EXAMPLE 87

NAc-Sar-Gly-NMe-D-Val-D-Ile-Thr-Nva-Ile-Arg-ProNH-ethyl

The desired product was prepared by substituting Fmoc-NMe-D-Val for Fmoc-Val and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-NMe-D-Val-D-Ile-Thr-Nva-Ile-Arg-ProNH-ethyl as trifluoroacetate salt; $R_t$=3.12 minutes (using a C-18 column and a solvent system increasing in gradient from 10% to 95% acetonitrile/water containing 0.01% TFA over a period of 10 minutes); MS (ESI) m/e 1008.7 (M+H); Amino Acid Anal.: 0.99 Pro; 1.02 Arg; 0.97 Nva; 0.43 Thr; 2.06 Ile; 0.96 Gly; 0.99 Sar.

EXAMPLE 88

NAc-Sar-Gly-Val-D-Ile-alloThr-NMeNle-Ile-Arg-ProNH-ethyl

The desired product was prepared by substituting Fmoc-alloThr(t-Bu) for Fmoc-Thr(t-Bu) and Fmoc-NMeNle for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-Ile-alloThr-NMeNle-Ile-Arg-ProNH-ethyl as trifluoroacetate salt; $R_t$=3.59 minutes (using a C-18 column and a solvent system increasing in gradient from 10% to 95% acetonitrile/water containing 0.01% TFA over a period of 10 minutes); MS (ESI) m/e 1022.8 (M+H); Amino Acid Anal.: 1.05 Pro; 0.97 Arg; 0.52 Thr; 1.88 Ile; 1.01 Gly; 1.03 Sar.

EXAMPLE 89

NAc-Sar-Gly-NMe-D-Phe-D-Ile-Thr-Nva-Ile-Arg-ProNH-ethyl

The desired product was prepared by substituting Fmoc-NMe-D-PheAla for Fmoc-Val and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-NMe-D-Phe-D-Ile-Thr-Nva-Ile-Arg-ProNH-ethyl as trifluoroacetate salt; $R_t$=3.32 minutes (using a C-18 column and a solvent system increasing in gradient from 10% to 95% acetonitrile/water containing 0.01% TFA over a period of 10 minutes); MS (ESI) m/e 1056.7 (M+H).

EXAMPLE 90

NAc-Sar-Gly-NMe-D-Phe-D-Ile-Thr-Nva-Ile-Arg-Pro-D-AlaNH$_2$

The desired product was prepared by substituting Fmoc-NMe-D-PheAla for Fmoc-Val and Fmoc-Nva for Fmoc-NMeNva in Example 28. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-NMe-D-Phe-D-Ile-Thr-Nva-Ile-Arg-Pro-D-AlaNH$_2$ as trifluoroacetate salt; $R_t$=3.18 minutes (using a C-18 column and a solvent system increasing in gradient from 10% to 95% acetonitrile/water containing 0.01% TFA over a period of 10 minutes); MS (ESI) m/e 1099.7 (M+H).

EXAMPLE 91

NAc-Sar-Gly-Val-D-Ile-Thr-Nva-NMeLeu-Arg-ProNH-ethyl

The desired product was prepared by substituting Fmoc-Nva for Fmoc-NMeNva and Fmoc-NMeLeu for Fmoc-Ile in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-Ile-Thr-Nva-NMeLeu-Arg-ProNH-ethyl as trifluoroacetate salt; $R_t$=3.39 minutes (using a C-18 column and a solvent system increasing in gradient from 10% to 95% acetonitrile/water containing 0.01% TFA over a period of 10 minutes); MS (ESI) m/e 1008.7 (M+H).

EXAMPLE 92

NAc-Sar-Gly-Asn-D-Leu-NMeSer-Nva-Ile-Arg-ProNH-ethyl

The desired product was prepared by substituting Fmoc-Asn(Trt) for Fmoc-Val, Fmoc-D-Leu for Fmoc-D-Ile, Fmoc-NMeSer(t-Bu) for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Asn-D-Leu-NMeSer-Nva-Ile-Arg-ProNH-ethyl as trifluoroacetate salt; $R_t$=2.28 minutes (using a C-18 column and a solvent system increasing in gradient from 10% to 95% acetonitrile/water containing 0.01% TFA over a period of 10 minutes); MS (ESI) m/e 1009.7 (M+H).

EXAMPLE 93

NAc-Sar-Gly-Val-D-alloIle-Ser-NMeSer-Ile-Arg-Pro-D-AlaNH$_2$

The desired product was prepared by substituting Fmoc-D-alloIle for Fmoc-D-Ile, Fmoc-Ser(t-Bu) for Fmoc-Thr(t-Bu) and Fmoc-NMeSer(t-Bu) for Fmoc-NMeNva in Example 28. Upon completion of the synthesis, cleavage of the resin-bound peptide, removal of the protecting groups, and precipitation with diethyl ether, the crude peptide as obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-alloIle-Ser-NMeSer-Ile-Arg-Pro-D-AlaNH$_2$ as trifluoroacetate salt; R$_t$=2.74 minutes (using a C-18 column and a solvent system increasing in gradient from 10% to 95% acetonitrile/water containing 0.01% TFA over a period of 10 minutes); MS (ESI) m/e 1025.7 (M+H).

EXAMPLE 94

NAc-Sar-Gly-Val-D-alloIle-NMeSer-Ser-Ile-Arg-ProNH-ethyl

The desired product was prepared by substituting Fmoc-D-alloIle for Fmoc-D-Ile, Fmoc-NMeSer(t-Bu) for Fmoc-Thr(t-Bu), and Fmoc-Ser(t-Bu) for Fmoc-NMeNva in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-alloIle-NMeSer-Ser-Ile-Arg-ProNH-ethyl as trifluoroacetate salt; R$_t$=2.53 minutes (using a C-18 column and a solvent system increasing in gradient from 10% to 95% acetonitrile/water containing 0.01% TFA over a period of 10 minutes); MS (ESI) m/e 982.6 (M+H).

EXAMPLE 95

NAc-Sar-Gly-Val-D-Ile-Thr-Nva-NMe-D-Ala-Arg-ProNH-ethyl

The desired product was prepared by substituting Fmoc-Nva for Fmoc-NMeNva and Fmoc-NMe-D-Ala for Fmoc-Ile in Example 1. Upon completion of the synthesis, cleavage of the resin-bound peptide, removal of the protecting groups, and precipitation with diethyl ether, the crude peptide was obtained. This was purified by preparative HPLC using a C-18 column and a solvent system increasing in gradient from 5% to 100% acetonitrile/water containing 0.01% TFA over a period of 50 minutes. The pure fractions were lyophilized to provide NAc-Sar-Gly-Val-D-Ile-Thr-Nva-NMe-D-Ala-Arg-ProNH-ethyl as trifluoroacetate salt; R$_t$=2.53 minutes (using a C-18 column and a solvent system increasing in gradient from 10% to 95% acetonitrile/water containing 0.01% TFA over a period of 10 minutes); MS (ESI) m/e 966.7 (M+H).

EXAMPLE 97

NAc-Sar-Gly-Val-D-alloIle-NMeTyr-Nva-Ile-Arg-ProNH-ethyl

The desired product can be prepared by substituting Fmoc-D-alloIle for Fmoc-D-Ile, Fmoc-NMeTyr(t-Bu) for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide NAc-Sar-Gly-Val-D-alloIle-NMeTyr-Nva-Ile-Arg-ProHEt as trifluoroacetate salt.

EXAMPLE 99

NAc-Sar-Gly-Val-D-Ile-Thr-NMeNva-D-Ile-Arg-ProNH-ethyl

The desired product can be prepared by substituting Fmoc-D-Ile for Fmoc-Ile in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide NAc-Sar-Gly-Val-D-Ile-Thr-NMeNva-D-Ile-Arg-ProNH-ethyl as trifluoroacetate salt.

EXAMPLE 100

NAc-Sar-Gly-Val-D-Ile-alloThr-NMeNva-Ile-Arg-ProNH-ethyl

The desired product can be prepared by substituting Fmoc-alloThr(t-Bu) for Fmoc-Thr(t-Bu) in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide NAc-Sar-Gly-Val-D-Ile-alloThr-NMeNva-Ile-Arg-ProNH-ethyl as trifluoroacetate salt.

EXAMPLE 101

NAc-Sar-Gly-Gln-D-Ile-Thr-NMeNva-D-Ile-Arg-ProNH-ethyl

The desired product can be prepared by substituting Fmoc-Gln(Trt) for Fmoc-Val and Fmoc-D-Ile for Fmoc-Ile in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide NAc-Sar-Gly-Gln-D-Ile-Thr-NMeNva-D-Ile-Arg-ProNH-ethyl as trifluoroacetate salt.

EXAMPLE 102

NAc-Sar-Gly-Val-D-Ile-Thr-NMeNva-D-Lys(Ac)-Arg-ProNH-ethyl

The desired product can be prepared by substituting Fmoc-D-Lys(Ac) for Fmoc-Ile in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide NAc-Sar-Gly-Val-D-Ile-Thr-NMeNva-D-Lys(Ac)-Arg-ProNH-ethyl as trifluoroacetate salt.

EXAMPLE 103

NAc-Sar-Gly-Gln-D-alloIle-NMeTyr-Nva-Ile-Arg-ProNH-ethyl

The desired product can be prepared by substituting Fmoc-Gln(Trt) for Fmoc-Val, Fmoc-D-alloIle for Fmoc-D-Ile, Fmoc-NMeTyr(t-Bu) for Fmoc-Thr(t-Bu), and Fmoc-Nva for Fmoc-NMeNva in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide NAc-Sar-Gly-Gln-D-alloIle-NMeTyr-Nva-Ile-Arg-ProNH-ethyl as trifluoroacetate salt.

EXAMPLE 104

NAc-Sar-Gly-Gln-D-alloIle-NMeTyr-Nva-D-Ile-Arg-ProNH-ethyl

The desired product can be prepared by substituting Fmoc-Gln(Trt) for Fmoc-Val, Fmoc-D-alloIle for Fmoc-D-Ile, Fmoc-NMeTyr(t-Bu) for Fmoc-Thr(t-Bu), Fmoc-Nva for Fmoc-NMeNva, and Fmoc-D-Ile for Fmoc-Ile in Example 1. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide NAc-Sar-Gly-Gln-D-alloIle-NMeTyr-Nva-D-Ile-Arg-ProNH-ethyl as trifluoroacetate salt.

EXAMPLE 105

NAc-Sar-Gly-Phe-D-Ile-Thr-NMeNva-Ile-Arg-Pro-D-AlaNH$_2$

The desired product can be prepared by substituting Fmoc-PheAla for Fmoc-Val in Example 28. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to provide NAc-Sar-Gly-Phe-D-Ile-Thr-NMeNva-Ile-Arg-Pro-D-AlaNH$_2$ as trifluoroacetate salt.

EXAMPLE 109

NMePro-Gly-Ile-D-Ile-Thr-NMeNva-Ile-Arg-ProNH-ethyl

The desired product can be prepared by substituting NMePro for Fmoc-Sar and Fmoc-Ile for Fmoc-Val in Example 1, and omitting the final coupling with acetic acid. Upon completion of the synthesis, cleavage of the resin-bound peptide, removal of the protecting groups, and precipitation with diethyl ether, the crude peptide can be obtained. This can be purified by preparative HPLC using a C-18 column and a solvent system increasing in gradient from 5% to 100% acetonitrile/water containing 0.01% TFA over a period of 50 minutes. The pure fractions can be lyophilized to NMePro-Gly-Ile-D-Ile-Thr-NmeNva-Ile-Arg-ProNH-ethyl as trifluoroacetate salt.

It will be evident to one skilled in the art that the instant invention is not limited to the forgoing illustrative examples, and that it can be embodied in other specific forms without departing from the essential attributes thereof. It is therefore desired that the examples be considered in all respects as illustrative and not restrictive, reference being made to the appended claims, and all changes which come within the meaning and range of equivalency of the claims and therefore intended to be embraced therein.

What is claimed is:

1. A compound having a formula:

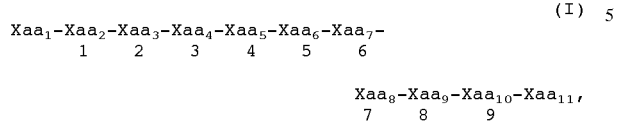

or a pharmaceutically acceptable salt thereof, wherein
at least one amide bond of an amino acid residue represented by $Xaa_3$, $Xaa_4$, $Xaa_5$, $Xaa_6$, $Xaa_7$, $Xaa_8$, $Xaa_9$, and $Xaa_{10}$ is N-alkylated;

$Xaa_1$ is selected from the group consisting of N-methylprolyl, and an acyl group, wherein the acyl group is selected from the group consisting of $R^1$—$(CH_2)_n$—$C(O)$—, wherein n is an integer from 0 to 8 and $R^1$ is selected from the group consisting of N-acetylamino, alkoxy, alkyl, aryl, carboxy, cycloalkenyl, cycloalkyl, heterocycle, and hydroxy; and
$R^2$—$CH_2CH_2$—$O$—$(CH_2CH_2O)_p$—$CH_2$—$C(O)$—, wherein p is an integer from 1 to 8 and $R^2$ is selected from the group consisting of hydrogen, N-acetylamino, and alkyl;

$Xaa_2$ is an N-alkylated amino acid selected from the group consisting of N-$(R^3)$-alanyl, N-$(R^3)$-glycyl, N-$(R^3)$-norvalyl, and N-$(R^3)$-prolyl, wherein $R^3$ is $C_1$–$C_5$-alkyl; or $Xaa_2$ is an N-unalkylated amino acid selected from the group consisting of
β-alanyl,
D-alanyl,
4-aminobutyryl,
(1R,3S)-1-aminocyclopentane-3-carbonyl,
(1S,3R)-1-aminocyclopentane-3-carbonyl,
(1R,4S)-1-aminocyclopent-2-ene-4-carbonyl,
(1S,4R)-1-aminocyclopent-2-ene-4-carbonyl,
asparaginyl,
3-(4-chlorophenyl)alanyl,
3-(4-cyanophenyl)alanyl,
glutaminyl,
glutamyl,
glycyl,
4-hydroxyprolyl,
3-(4-methylphenyl)alanyl,
prolyl,
seryl, and
threonyl;

$Xaa_3$ is an N-alkylated amino acid selected from the group consisting of N-$(R^3)$-alanyl, N-$(R^3)$-glycyl, N-$(R^3)$-leucyl, and N-$(R^3)$-phenylalanyl, wherein $R^3$ is as defined above; or $Xaa_3$ is an N-unalkylated amino acid selected from the group consisting of
alanyl,
(1S,3R)-1-aminocyclopentane-3-carbonyl,
(1S,4R)-1-aminocyclopent-2-ene-4-carbonyl,
asparaginyl,
aspartyl,
3-(3-cyanophenyl)alanyl,
3-(4-cyanophenyl)alanyl,
glutaminyl,
glycyl,
leucyl,
lysyl(N-epsilon-acetyl),
3-(4-methylphenyl)alanyl,
norvalyl,
prolyl, and
phenylalanyl;

$Xaa_4$ is an N-alkylated amino acid selected from the group consisting of N-$(R^3)$-alanyl, N-$(R^3)$-glycyl, N-$(R^3)$-homophenylalanyl, N-$(R^3)$-isoleucyl, N-$(R^3)$-leucyl, N-$(R^3)$-norvalyl, N-$(R^3)$-phenylalanyl, N-$(R^3)$-D-phenylalanyl, N-$(R^3)$-seryl, N-$(R^3)$-tyrosyl, N-$(R^3)$-valyl, and N-$(R^3)$-D-valyl, wherein $R^3$ is as defined above; or $Xaa_4$ is an N-unalkylated amino acid selected from the group consisting of
alanyl,
alloisoleucyl,
allylglycyl,
2-aminobutyryl,
(1R,4S)-aminocyclopent-2-ene-4-carbonyl,
asparaginyl,
aspartyl,
3-[2-(5-bromothienyl)]alanyl,
3-(3-chlorophenyl)alanyl,
3-(4-chlorophenyl)alanyl,
3-(3-cyanophenyl)alanyl,
cyclohexylalanyl,
3-(3,4-dimethoxyphenyl)alanyl,
3-(3-fluorophenyl)alanyl,
3-(4-fluorophenyl)alanyl,
glutaminyl,
glycyl,
histidyl,
homophenylalanyl,
homoseryl,
isoleucyl,
leucyl,
lysyl(N-epsilon-acetyl),
methionyl,
methionyl(sulfone),
3-(4-methylphenyl)alanyl,
3-(naphth-1-yl)alanyl,
3-(naphth-2-yl)alanyl,
norornithyl,
norvalyl,
phenyalanyl,
phenylglycyl,
prolyl,
3-(3-pyridyl)alanyl,
3-(4-thiazolyl)alanyl,
3-(2-thienyl)alanyl,
seryl,
seryl(O-benzyl),
styrylalanyl,
tryptyl,
tyrosyl,
valyl, and
D-valyl;

$Xaa_5$ is an N-alkylated amino acid selected from the group consisting of N-$(R^3)$-D-homophenylalanyl, N-$(R^3)$-D-isoleucyl, N-$(R^3)$-D-leucyl, and N-$(R^3)$-D-phenylalanyl, wherein $R^3$ is as defined above; or $Xaa_5$ is an N-unalkylated amino acid selected from the group consisting of
D-alanyl,
alloisoleucyl,
D-alloisoleucyl,
D-2-aminobutyryl,
D-3-(4-aminophenyl)alanyl,
D-asparaginyl,
D-3-(3-benzothienyl)alanyl,
D-t-butylglycyl, D-(chlorophenyl)alanyl,
D-citrullyl,
D-3-(3-cyanophenyl)alanyl,
D-cyclohexylalanyl,
cyclohexylglycyl,
D-cysteinyl(S-acetamidomethyl),
D-cysteinyl(S-t-butyl),
D-3-(3,4-difluorophenyl)alanyl,
D-(3,4-dimethoxyphenyl)alanyl,
D-glutaminyl,
glycyl,
D-homophenylalanyl,
D-homoseryl,
isoleucyl,
D-isoleucyl,
D-leucyl,
D-lysyl(N-epsilon-nicotinyl),
D-lysyl,
D-methionyl,
D-3-(4-methylphenyl)alanyl,
D-3-(naphth-1-yl)alanyl,
D-3-(naphth-2-yl)alanyl,
D-3-(4-nitrophenyl)alanyl,
D-norleucyl,
D-ornithyl,
D-penicillaminyl(S-acetamidomethyl),
D-penicillaminyl(S-benzyl),
D-penicillaminyl(S-methyl),
D-penicillaminyl,
D-3-(pentafluorophenyl)alanyl,
D-phenylalanyl,
D-prolyl,
D-seryl(O-benzyl),
D-seryl,
D-(2-thienyl)alanyl,
D-threonyl(O-benzyl),
D-threonyl,
D-3-(3-trifluoromethylphenyl)alanyl,
D-(3,4,5-trifluorophenyl)alanyl,
D-tryptyl,
D-tyrosyl(O-ethyl),
D-tyrosyl, and
D-valyl;
Xaa$_6$ is an N-alkylated amino acid selected from the group consisting of N-($R^3$)-aspartyl, N-($R^3$)-glutamyl, N-($R^3$)-glycyl, N-($R^3$)-seryl, N-($R^3$)-threonyl, N-($R^3$)-threonyl(O-benzyl), and N-($R^3$)-tyrosyl, wherein $R^3$ is as defined above; or Xaa$_6$ is an N-unalkylated amino acid selected from the group consisting of
alanyl,
allothreonyl,
D-allothreonyl,
allylglycyl,
asparaginyl,
aspartyl,
glutaminyl,
glycyl,
histidyl,
homoseryl,
D-homoseryl,
3-(4-hydroxymethylphenyl)alanyl,
isoleucyl,
lysyl(N-epsilon-acetyl),
methionyl,
3-(naphth-2-yl)alanyl,
norvalyl,
octylglycyl,
prolyl,
3-(3-pyridyl)alanyl,
seryl,
D-seryl,
threonyl,
D-threonyl,
tryptyl,
tyrosyl, and
tyrosyl(O-methyl);
Xaa$_7$ is an N-alkylated amino acid selected from the group consisting of N-($R^3$)-alanyl, N-($R^3$)-glycyl, N-($R^3$)-isoleucyl, N-($R^3$)-leucyl, N-($R^3$)-D-leucyl, N-($R^3$)-norleucyl, N-($R^3$)-norvalyl, N-($R^3$)-seryl, N-($R^3$)-threonyl, and N-($R^3$)-valyl, wherein $R^3$ is as defined above; or Xaa$_7$ is an N-unalkylated amino acid selected from the group consisting of
alanyl,
allothreonyl,
allylglycyl,
3-(4-amidophenyl)alanyl,
2-aminobutyryl,
arginyl,
asparaginyl,
cyclohexylalanyl,
glutaminyl,
D-glutaminyl,
glycyl,
homoalanyl,
homoseryl,
4-hydroxyprolyl,
leucyl,
D-leucyl,
lysyl(N-epsilon-acetyl),
methionyl sulfone,
methionyl sulfoxide,
methionyl,
norleucyl,
norvalyl,
D-norvalyl,
octylglycyl,
ornithyl(N-delta-acetyl),
phenylalanyl,
propargylglycyl,
seryl,
D-seryl,
threonyl,
tryptyl,
tyrosyl, and
valyl;
Xaa$_8$ is an N-alkylated amino acid selected from the group consisting of N-($R^3$)-alanyl, N-($R^3$)-D-alanyl, N-($R^3$)-isoleucyl, and N-($R^3$)-leucyl, wherein $R^3$ is as defined above; or Xaa$_8$ is an N-unalkylated amino acid selected from the group consisting of
alanyl,
alloisoleucyl,
D-alloisoleucyl,
allylglycyl,
citrullyl,
glycyl,
isoleucyl,
D-isoleucyl,
leucyl,
D-leucyl,
lysyl(N-epsilon-acetyl),
D-lysyl(N-epsilon-acetyl),
methionyl, 3-(naphth-1-yl)alanyl,
norvalyl,
prolyl,
D-prolyl, and
valyl;

Xaa$_9$ is the N-alkylated amino acid N-(R$^3$)-arginyl, wherein R$^3$ is as defined above; or Xaa$_9$ is an N-unalkylated amino acid selected from the group consisting of
[(4-amino-N-isopropyl)cyclohexyl]alanyl,
3-(4-amino-N-isopropylphenyl)alanyl,
arginyl(N$^G$N$^{G'}$ diethyl),
arginyl,
D-arginyl,
citrullyl,
glutaminyl,
3-(4-guanidinophenyl)alanyl,
histidyl,
homoarginyl,
lysyl(N-epsilon-isopropyl),
lysyl(N-epsilon-nicotinyl),
lysyl,
norarginyl,
ornithyl,
ornithyl[N-delta-(2-imidazolinyl)],
ornithyl(N-delta-isopropyl), and
3-(3-pyridyl)alanyl;

Xaa$_{10}$ is an N-alkylated amino acid selected from the group consisting of N-(R$^3$)-alanyl, N-(R$^3$)-D-alanyl, N-(R$^3$)-glycyl, N-(R$^3$)-homoalanyl, and N-(R$^3$)-norvalyl, wherein R$^3$ is as defined above; or Xaa$_{10}$ is an N-unalkylated amino acid selected from the group consisting of
D-alanyl,
2-aminobutyryl,
D-2-aminobutyryl,
2-aminoisobutyryl,
3,4-dehydroprolyl,
4-hydroxyprolyl,
phenylalanyl,
prolyl,
D-prolyl,
1,2,3,4-tetrahydroisoquinoline-3-carbonyl, and
D-valyl; and Xaa$_{11}$ is a hydroxy group or an amino acid amide selected from the group consisting of:
alanylamide,
D-alanylamide,
alanylethylamide,
D-alanylethylamide,
azaglycylamide,
glycylamide,
glycylethylamide,
lysyl(N-epsilon-acetyl),
D-lysyl(N-epsilon-acetyl),
N-methyl-D-alanylamide,
sarcosylamide,
serylamide,
D-serylamide,
a residue represented by the formula

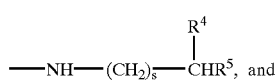

and
a group represented by the formula —NH—R$^6$; wherein s is an integer from 0 to 8;
R$^4$ is selected from the group consisting of hydrogen, alkyl, and a 5- to 6-membered cycloalkyl ring;
R$^5$ is selected from the group consisting of hydrogen, alkoxy, alkyl, aryl, cycloalkenyl, cycloalkyl, heterocycle, and hydroxy;
provided that s is not zero when R$^5$ is hydroxy or alkoxy; and
R$^6$ is selected from hydrogen and hydroxy.

2. A compound according to claim 1, wherein Xaa$_1$ is selected from the group consisting of
acetyl,
N-acetyl-β-alanyl,
butyryl,
(4-N-acetylamino)butyryl,
(6-N-acetylamino)caproyl,
(8-N-acetylamino)-3,6-dioxo-octanoyl,
caproyl,
5-chloro-2-hydroxynicotinyl,
5-chloro-6-hydroxynicotinyl,
2-chloroisonicotinyl,
2-chloro-6-methylnicotinyl,
cyclohexylacetyl,
furoyl,
2-hydroxy-6-methylnicotinyl,
6-hydroxynicotinyl,
6-hydroxy-2-picolinyl,
isonicotinyl,
2-methoxyacetyl,
2-methylnicotinyl,
6-methylnicotinyl,
(4-methyl)phenylacetyl,
N-methylprolyl,
nicotinyl,
phenylacetyl,
propionyl,
shikimyl,
succinyl, and
tetrahydrofuroyl.

3. A compound according to claim 2, wherein Xaa$_1$ is selected from the group consisting of
acetyl,
N-methylprolyl, and
succinyl.

4. A compound according to claim 1, wherein Xaa$_2$ is selected from the group consisting of
N-methylalanyl,
sarcosyl,
N-ethylglycyl,
N-methylnorvalyl,
N-methylprolyl,
β-alanyl,
4-aminobutyryl,
asparaginyl,
glutaminyl,
glutamyl,
glycyl,
prolyl,
seryl, and threonyl.

5. A compound according to claim 4, wherein $Xaa_2$ is selected from the group consisting of
sarcosyl, and
N-methylprolyl.

6. A compound according to claim 1, wherein $Xaa_3$ is selected from the group consisting of
N-methylalanyl,
sarcosyl,
N-methylleucyl,
N-methylphenylalanyl,
alanyl,
asparaginyl,
aspartyl,
glutaminyl,
glycyl,
leucyl,
norvalyl,
prolyl, and
phenylalanyl.

7. A compound according to claim 6, wherein $Xaa_3$ is selected from the group consisting of
N-methylalanyl, and
glycyl.

8. A compound according to claim 1, wherein $Xaa_4$ is selected from the group consisting of
N-methylalanyl,
sarcosyl,
N-methylhomophenylalanyl,
N-methylisoleucyl,
N-methylleucyl,
N-methylnorvalyl,
N-methylphenylalanyl,
N-methyl-D-phenylalanyl,
N-methylseryl,
N-methyltyrosyl,
N-methylvalyl,
N-methyl-D-valyl,
3-[2-(5-bromothienyl)]alanyl,
3-(3-chlorophenyl)alanyl,
3-(4-chlorophenyl)alanyl,
3-(3-cyanophenyl)alanyl,
3-(3,4-dimethoxyphenyl)alanyl,
3-(3-fluorophenyl)alanyl,
3-(4-fluorophenyl)alanyl,
3-(4-methylphenyl)alanyl,
3-(naphth-1-yl)alanyl,
3-(naphth-2-yl)alanyl,
3-(3-pyridyl)alanyl,
3-(4-thiazolyl)alanyl,
3-(2-thienyl)alanyl,
alloisoleucyl,
allylglycyl,
2-aminobutyryl,
asparaginyl,
cyclohexylalanyl,
glutaminyl,
glycyl,
histidyl,
homophenylalanyl,
homoseryl,
isoleucyl,
leucyl,
lysyl(N-epsilon-acetyl),
methionyl,
methionyl(sulfone),
norornithyl,
norvalyl,
phenylalanyl,
phenylglycyl,
prolyl,
seryl,
seryl(O-benzyl),
styrylalanyl,
tryptyl,
tyrosyl, and
valyl.

9. A compound according to claim 8, wherein $Xaa_4$ is selected from the group consisting of
N-methylalanyl,
N-methylisoleucyl,
N-methylleucyl,
N-methylnorvalyl,
N-methylphenylalanyl,
N-methyl-D-phenylalanyl,
N-methylvalyl,
N-methyl-D-valyl,
asparaginyl,
glutaminyl,
isoleucyl,
phenylalanyl, and
valyl.

10. A compound according to claim 1, wherein $Xaa_5$ is selected from the group consisting of
N-methyl-D-homophenylalanyl,
N-methyl-D-isoleucyl,
N-methyl-D-leucyl,
D-3-(4-aminophenyl)alanyl,
D-3-(3-benzothienyl)alanyl,
D-(chlorophenyl)alanyl,
D-3-(3-cyanophenyl)alanyl,
D-3-(3,4-difluorophenyl)alanyl,
D-(3,4-dimethoxyphenyl)alanyl,
D-3-(4-methylphenyl)alanyl,
D-3-(naphth-1-yl)alanyl,
D-3-(naphth-2-yl)alanyl.
D-3-(4-nitrophenyl)alanyl,
D-3-(pentafluorophenyl)alanyl,
D-3-(3-trifluoromethylphenyl)alanyl,
D-(3,4,5-trifluorophenyl)alanyl,
D-alanyl,
alloisoleucyl,
D-alloisoleucyl,
D-2-aminobutyryl,
D-asparaginyl, D-citrullyl,
D-cyclohexylalanyl,
cyclohexylglycyl,
D-cysteinyl(S-acetamidomethyl),
D-cysteinyl(S-t-butyl),
D-glutaminyl,
glycyl,
D-homophenylalanyl,
D-homoseryl,
isoleucyl,
D-isoleucyl,
D-leucyl,
D-lysyl(N-epsilon-nicotinyl),
D-lysyl,
D-methionyl,
D-norleucyl,
D-ornithyl,
D-penicillaminyl(S-acetamidomethyl),
D-penicillaminyl(S-benzyl),
D-penicillaminyl(S-methyl),
D-penicillaminyl,
D-phenylalanyl,
D-prolyl,
D-seryl(O-benzyl),
D-seryl,
D-t-butylglycyl,
D-(2-thienyl)alanyl,
D-threonyl(O-benzyl),
D-threonyl,
D-tryptyl,
D-tyrosyl(O-ethyl),
D-tyrosyl, and
D-valyl.

11. A compound according to claim 10, wherein $Xaa_5$ is selected from the group consisting of
N-methyl-D-leucyl,
D-alloisoleucyl,
D-isoleucyl,
D-leucyl,
D-homophenylalanyl, and
D-penacillaminyl(S-methyl).

12. A compound according to claim 1, wherein $Xaa_6$ is selected from the group consisting of
N-methylaspartyl,
N-methylglutamyl,
sarcosyl,
N-methylseryl,
N-methyltyrosyl,
N-methylthreonyl,
N-methylthreonyl(O-benzyl),
alanyl,
3-(4-hydroxymethylphenyl)alanyl,
3-(naphth-2-yl)alanyl,
3-(3-pyridyl)alanyl,
allothreonyl,
D-allothreonyl,
allylglycyl,
glutaminyl,
glycyl,
histidyl,
homoseryl,
D-homoseryl,
isoleucyl,
methionyl,
norvalyl,
octylglycyl,
prolyl,
seryl,
D-seryl,
threonyl,
D-threonyl,
tryptyl, and
tyrosyl.

13. A compound according to claim 12, wherein $Xaa_6$ is selected from the group consisting of
N-methylaspartyl,
N-methylglutamyl,
sarcosyl,
N-methylseryl,
N-methyltyrosyl,
N-methylthreonyl,
N-methylthreonyl(O-benzyl),
allothreonyl,
seryl,
threonyl, and
tyrosyl.

14. A compound according to claim 1, wherein $Xaa_7$ is selected from the group consisting of
N-methylalanyl,
sarcosyl,
N-methylisoleucyl,
N-methylleucyl,
N-methyl-D-leucyl,
N-methylnorleucyl,
N-methylnorvalyl,
N-methylseryl,
N-methylthreonyl,
N-methylvalyl,
alanyl,
allylglycyl,
3-(4-amidophenyl)alanyl,
2-aminobutyryl,
arginyl,
asparaginyl,
cyclohexylalanyl,
glutaminyl,
D-glutaminyl,
glycyl,
homoalanyl,
homoseryl,
leucyl,
D-leucyl,
lysyl(N-epsilon-acetyl),
methionyl, methionyl sulfone,
methionyl sulfoxide,
norleucyl,
norvalyl,
D-norvalyl,
octylglycyl,
ornithyl(N-delta-acetyl),
phenylalanyl,
propargylglycyl,
seryl,
D-seryl,
tyrosyl, and
valyl.

15. A compound according to claim 14, wherein $Xaa_7$ is selected from the group consisting of
N-methylalanyl,
sarcosyl,
N-methylisoleucyl,
N-methylleucyl,
N-methyl-D-leucyl,
N-methylnorleucyl,
N-methylnorvalyl,
N-methylseryl,
N-methylthreonyl,
N-methylvalyl,
norleucyl,
norvalyl, and
seryl.

16. A compound according to claim 1, wherein $Xaa_8$ is selected from the group consisting of
N-methylalanyl,
N-methyl-D-alanyl,
N-methylisoleucyl,
N-methylleucyl,
3-(naphth-1-yl)alanyl,
alanyl,
allylglycyl,
glycyl,
isoleucyl,
D-isoleucyl,
leucyl,
D-lysyl(N-epsilon-acetyl),
methionyl,
norvalyl,
prolyl, and
valyl.

17. A compound according to claim 16, wherein $Xaa_8$ is selected from the group consisting of
N-methylalanyl,
N-methyl-D-alanyl,
N-methylisoleucyl,
N-methylleucyl,
isoleucyl,
D-isoleucyl, and
D-lysyl(N-epsilon-acetyl).

18. The compound according to claim 1, wherein $Xaa_9$ is selected from the group consisting of
N-methylarginyl,
[(4-amino-N-isopropyl)cyclohexyl]alanyl,
3-(4-amino-N-isopropylphenyl)alanyl,
3-(4-guanidinophenyl)alanyl,
arginyl,
arginyl($N^G N^{G'}$ diethyl),
citrullyl,
2-[4-piperidinyl(N-amidino)]glycyl,
glutaminyl,
histidyl,
homoarginyl,
lysyl,
lysyl(N-epsilon-isopropyl),
lysyl(N-epsilon-nicotinyl),
norarginyl,
ornithyl,
ornithyl[N-delta-(2-imidazolinyl)], and
ornithyl(N-delta-isopropyl).

19. A compound according to claim 18, wherein $Xaa_9$ is selected from the group consisting of
arginyl, and
N-methylarginyl.

20. A compound according to claim 1, wherein $Xaa_{10}$ is selected from the group consisting of
N-methylalanyl,
sarcosyl,
N-methylhomoalanyl,
N-methylnorvalyl,
D-alanyl,
2-aminobutyryl,
2-aminoisobutyryl,
3,4-dehydroprolyl,
4-hydroxyprolyl,
phenylalanyl,
prolyl,
D-prolyl, and
1,2,3,4-tetrahydroisoquinoline-3-carbonyl.

21. A compound according to claim 20, wherein $Xaa_{10}$ is selected from the group consisting of
N-methylalanyl,
sarcosyl,
N-methylnorvalyl, and
prolyl.

22. A compound according to claim 1, wherein $Xaa_{11}$ is selected from the group consisting of
alanylamide,
D-alanylamide,
alanylethylamide,
D-alanylethylamide,
azaglycylamide,
NH-cyclobutyl,
NH-cycloheptyl,
NH-1-(cyclohexyl)ethyl,
NH-2-(cyclohexyl)ethyl,
NH-2-(ethoxy)ethyl,
NH-ethyl,
NH-glycyl,
glycylethylamide,
NH-hexyl, NH-2-(hydroxy)ethyl,
NH-isoamyl,
NH-isobutyl,
NH-2-(isopropoxy)ethyl,
NH-isopropyl,
lysyl(N-epsilon-acetyl),
D-lysyl(N-epsilon-acetyl),
NH-2-(methoxy)ethyl,
NH-3-(methoxy)propyl,
N-methyl-D-alanylamide,
NH-propyl,
NH-2-(1-pyrrolidine)ethyl,
sarcosylamide,
serylamide, and
D-serylamide.

23. A compound according to claim 22, wherein $Xaa_{11}$ is selected from the group consisting of
NH-ethyl, and
D-alanylamide.

24. A compound according to claim 1, wherein
$Xaa_1$ is selected from the group consisting of
acetyl,
N-methylprolyl, and
succinyl;
$Xaa_2$ is selected from the group consisting of
sarcosyl, and
N-methylprolyl;
$Xaa_3$ is selected from the group consisting of
N-methylalanyl, and
glycyl;
$Xaa_4$ is selected from the group consisting of
N-methylalanyl,
N-methylisoleucyl,
N-methylleucyl,
N-methylnorvalyl,
N-methylphenylalanyl,
N-methyl-D-phenylalanyl,
N-methylvalyl,
N-methyl-D-valyl,
asparaginyl,
glutaminyl,
isoleucyl,
phenylalanyl, and
valyl;
$Xaa_5$ is selected from the group consisting of
N-methyl-D-leucyl,
D-alloisoleucyl,
D-isoleucyl,
D-leucyl,
D-homophenylalanyl, and
D-penacillaminyl(S-methyl);
$Xaa_6$ is selected from the group consisting of
N-methylaspartyl,
N-methylglutamyl,
sarcosyl,
N-methylseryl,
N-methyltyrosyl,
N-methylthreonyl,
N-methylthreonyl(O-benzyl),
allothreonyl,
seryl,
threonyl, and
tyrosyl;
$Xaa_7$ is selected from the group consisting of
N-methylalanyl,
sarcosyl,
N-methylisoleucyl,
N-methylleucyl,
N-methyl-D-leucyl,
N-methylnorleucyl,
N-methylnorvalyl,
N-methylseryl,
N-methylthreonyl,
N-methylvalyl,
norleucyl,
norvalyl, and
seryl;
$Xaa_8$ is selected from the group consisting of
N-methylalanyl,
N-methyl-D-alanyl,
N-methylisoleucyl,
N-methylleucyl,
isoleucyl,
D-isoleucyl, and
D-lysyl(N-epsilon-acetyl);
$Xaa_9$ is selected from the group consisting of
arginyl, and
N-methylarginyl;
$Xaa_{10}$ is selected from the group consisting of
N-methylalanyl,
sarcosyl,
N-methylnorvalyl, and
prolyl; and
$Xaa_{11}$ is selected from the group consisting of
NH-ethyl, and
D-alanylamide.

25. A compound according to claim 24 wherein $Xaa_1$ is selected from the group consisting of
acetyl, and
succinyl.

26. A compound according to claim 24 wherein $Xaa_2$ is sarcosyl.

27. A compound according to claim 24 wherein $Xaa_4$ is selected from the group consisting of
N-methylleucyl,
N-methylnorvalyl,
N-methylphenylalanyl,
N-methyl-D-phenylalanyl, and
valyl.

28. A compound according to claim 24 wherein $Xaa_5$ is selected from the group consisting of
N-methyl-D-leucyl,
D-alloisoleucyl,
D-isoleucyl, and p1 D-leucyl.

29. A compound according to claim 24 wherein $Xaa_6$ is selected from the group consisting of
sarcosyl,
N-methylseryl,
N-methyltyrosyl,
allothreonyl,
seryl, and
threonyl.

30. A compound according to claim 24 wherein $Xaa_7$ is selected from the group consisting of
N-methylalanyl,
N-methylnorvalyl, N-methylvalyl, and norvalyl.

31. A compound according to claim 24 wherein $Xaa_8$ is selected from the group consisting of N-methylleucyl, and isoleucyl.

32. A compound according to claim 24 wherein $Xaa_9$ is arginyl.

33. A compound according to claim 24 wherein $Xaa_{10}$ is selected from the group consisting of N-methylalanyl, and prolyl.

34. A composition comprising a compound of claim 1 and a pharmaceutically acceptable carrier.

35. A compound, or a pharmaceutically acceptable salt thereof, selected from the group consisting of N-Ac-Sar-Gly-Val-D-Ile-Thr-Nva-Ile-Arg-SarNH-ethyl,
N-Succinyl-Sar-Gly-Val-D-Leu-Thr-NMeNva-Ile-Arg-ProNH-ethyl,
N-Ac-Sar-Gly-Val-D-Ile-Thr-Nva-Ile-NMeArg-ProNH-ethyl,
N-Ac-Sar-Gly-NMeVal-D-Ile-Thr-Nva-Ile-Arg-ProNH-ethyl,
N-Ac-Sar-Gly-NMeIle-D-Ile-Thr-Nva-Ile-Arg-ProNH-ethyl,
N-Ac-Sar-Gly-NMeAla-D-Ile-Thr-Nva-Ile-Arg-ProNH-ethyl,
N-MePro-Sar-Gly-Val-D-Ile-Thr-Nva-Ile-Arg-ProNH-ethyl,
N-Ac-Sar-Gly-Val-D-Ile-NMeThr(Bzl)-Nva-Ile-Arg-ProNH-ethyl,
N-Ac-Sar-Gly-Val-D-Ile-Thr-Sar-Ile-Arg-ProNH-ethyl,
N-Ac-Sar-Gly-Val-D-Ile-Thr-NMeLeu-Ile-Arg-ProNH-ethyl,
N-Ac-Sar-Gly-Val-D-alloIle-Thr-NMeVal-Ile-Arg-ProNH-ethyl,
N-Ac-Sar-Gly-Val-D-Ile-Thr-NMeVal-Ile-Arg-Pro-D-AlaNH$_2$,
N-Ac-Sar-Gly-Val-D-Ile-NMeThr-Nva-Ile-Arg-ProNH-ethyl,
N-Ac-Sar-Gly-Val-D-alloIle-Thr-NMeSer-Ile-Arg-Pro-D-AlaNH$_2$,
N-Ac-Sar-Gly-Phe-D-Ile-Thr-NMeVal-Ile-Arg-Pro-D-AlaNH$_2$,
N-Ac-Sar-Gly-Val-D-alloIle-Tyr-NMeNva-Ile-Arg-ProNH-ethyl,
N-Ac-Sar-Gly-Val-D-alloIle-Tyr-NMeVal-Ile-Arg-ProNH-ethyl,
N-Ac-Sar-Gly-Gln-D-Ile-Thr-NMeNva-Ile-Arg-Pro-D-AlaNH$_2$,
N-Ac-Sar-Gly-Val-D-alloIle-NMeThr-Nva-Ile-Arg-ProNH-ethyl,
N-Ac-Sar-Gly-Val-D-Ile-Thr-NMeSer-Ile-Arg-Pro-D-AlaNH$_2$,
N-Ac-Sar-Gly-NMeVal-D-Ile-Thr-Nva-Ile-Arg-Pro-D-AlaNH$_2$,
N-Ac-Sar-Gly-NMeVal-D-alloIle-Thr-Nva-Ile-Arg-ProNH-ethyl,
N-Ac-Sar-Gly-Val-D-Hphe-Thr-NMeNva-Ile-Arg-ProNH-ethyl,
N-Ac-Sar-Gly-Val-D-Hphe-Thr-NMeVal-Ile-Arg-ProNH-ethyl,
N-Ac-Sar-Gly-Val-D-Pen(SMe)-Thr-NMeNva-Ile-Arg-ProNH-ethyl,
N-Ac-Sar-Gly-Val-D-Pen(SMe)-Thr-NMeVa-Ile-Arg-ProNH-ethyl,
NAc-Sar-Gly-Val-D-Ile-Thr-Nva-Ile-Arg-NMeNvaNH-ethyl,
NAc-Sar-Gly-Val-NMe-D-Leu-Ser-Nva-Ile-Arg-ProNH-ethyl,
NAc-Sar-Gly-Asn-NMe-D-Leu-Ser-Nva-Ile-Arg-ProNH-ethyl,
NAc-Sar-Gly-Asn-D-Leu-NMeSer-Nva-Ile-Arg-ProNH-ethyl,
NAc-Sar-Gly-Val-D-alloIle-NMeSer-Nva-Ile-Arg-ProNH-ethyl,
NAc-Sar-Gly-Val-D-Ile-Thr-NMeNle-Ile-Arg-ProNH-ethyl,
NAc-Sar-Gly-Val-D-Ile-Sar-Nva-Ile-Arg-ProNH-ethyl,
NAc-Sar-Gly-Val-D-alloIle-Sar-Nva-Ile-Arg-ProNH-ethyl,
NAc-Sar-Gly-Val-D-Ile-Thr-Nva-NMeAla-Arg-ProNH-ethyl,
NAc-Sar-Gly-Val-D-Ile-NMeAsp-Nva-Ile-Arg-ProNH-ethyl,
NAc-Sar-Gly-Val-D-Ile-Thr-NMe-D-Leu-Ile-Arg-ProNH-ethyl,
NAc-Sar-Gly-Val-D-Ile-NMeGlu-Nva-Ile-Arg-ProNH-ethyl,
NAc-Sar-Gly-NMe-D-Val-D-Ile-Thr-Nva-Ile-Arg-ProNH-ethyl,
NAc-Sar-Gly-NMe-D-Phe-D-Ile-Thr-Nva-Ile-Arg-Pro-D-AlaNH$_2$,
NAc-Sar-Gly-Val-D-Ile-Thr-Nva-NMeLeu-Arg-ProNH-ethyl,
NAc-Sar-Gly-Asn-D-Leu-NMeSer-Nva-Ile-Arg-ProNH-ethyl,
NAc-Sar-Gly-Val-D-alloIle-NMeSer-Ser-Ile-Arg-ProNH-ethyl,
NAc-Sar-Gly-Val-D-Ile-Thr-Nva-NMe-D-Ala-Arg-ProNH-ethyl,
NAc-Sar-Gly-Val-D-Ile-Thr-NMeNva-D-Ile-Arg-ProNH-ethyl,
NAc-Sar-Gly-Val-D-Ile-alloThr-NMeNva-Ile-Arg-ProNH-ethyl,
NAc-Sar-Gly-Gln-D-Ile-Thr-NMeNva-D-Ile-Arg-ProNH-ethyl,
NAc-Sar-Gly-Gln-D-alloIle-NMeTyr-Nva-Ile-Arg-ProNH-ethyl,
NAc-Sar-Gly-Gln-D-alloIle-NMeTyr-Nva-D-Ile-Arg-ProNH-ethyl, and
NAc-Sar-Gly-Phe-D-Ile-Thr-NMeNva-Ile-Arg-Pro-D-AlaNH$_2$.

36. A compound or a pharmaceutically acceptable salt thereof, selected from the group consisting of N-Ac-Sar-Gly-Val-D-Ile-Thr-NMeNva-Ile-Arg-ProNH-ethyl,
N-Ac-Sar-Gly-Val-D-Ile-Thr-Nva-NMeIle-Arg-ProNH-ethyl,
N-Ac-Sar-Gly-Val-D-Ile-Thr-NMeAla-Ile-Arg-ProNH-ethyl,
N-Ac-Sar-Gly-Val-D-Ile-Thr-NMeVal-Ile-Arg-ProNH-ethyl,
N-Ac-Sar-Gly-Val-D-Ile-Thr-Nva-Ile-Arg-NMeAlaNH-ethyl,
N-Succinyl-Sar-Gly-Val-D-Ile-Thr-NMeNva-Ile-Arg-ProNH-ethyl,
N-Ac-Sar-NMeAla-Val-D-Ile-Thr-Nva-Ile-Arg-ProNH-ethyl,
N-Ac-Sar-Gly-NMePhe-D-Ile-Thr-Nva-Ile-Arg-ProNH-ethyl,
N-Ac-Sar-Gly-NMeNva-D-Ile-Thr-Nva-Ile-Arg-ProNH-ethyl,
N-Ac-Sar-Gly-Val-D-Leu-Sar-Nva-Ile-Arg-ProNH-ethyl, N-Ac-Sar-Gly-NMeLeu-D-Ile-Thr-Nva-Ile-Arg-ProNH-ethyl,
N-Ac-Sar-Gly-Val-D-alloIle-Thr-NMeNva-Ile-Arg-ProNH-ethyl,
N-Ac-Sar-Gly-Val-D-Ile-Thr-NMeNva-Ile-Arg-Pro-D-AlaNH$_2$,
N-Ac-Sar-Gly-Val-D-Ile-NMeSer-Nva-Ile-Arg-ProNH-ethyl,
N-Ac-Sar-Gly-Val-D-Leu-NMeSer-Nva-Ile-Arg-ProNH-ethyl,
N-Ac-Sar-Gly-Val-D-Leu-Ser-NMeNva-Ile-Arg-ProNH-ethyl,
N-Ac-Sar-Gly-Val-D-alloIle-Ser-NMeSer-Ile-Arg-ProNH-ethyl,
N-Ac-Sar-Gly-Val-D-alloIle-Thr-NMeSer-Ile-Arg-ProNH-ethyl,
N-Ac-Sar-Gly-Val-D-Ile-Thr-NMeSer-Ile-Arg-ProNH-ethyl,
N-Ac-Sar-Gly-Val-D-alloIle-NMeSer-Ser-Ile-Arg-ProNH-ethyl,
NAc-Sar-Gly-Val-NMe-D-Leu-Thr-Nva-Ile-Arg-ProNH-ethyl,
NAc-Sar-Gly-NMeNva-D-alloIle-Thr-Nva-Ile-Arg-ProNH-ethyl,
NAc-Sar-Gly-NMePhe-D-Ile-Thr-Nva-Ile-Arg-Pro-D-AlaNH$_2$,
NAc-Sar-Gly-Val-D-Ile-alloThr-NMeNle-Ile-Arg-ProNH-ethyl,
NAc-Sar-Gly-NMe-DPhe-D-Ile-Thr-Nva-Ile-Arg-ProNH-ethyl,
NAc-Sar-Gly-Val-D-alloIle-Ser-NMeSer-Ile-Arg-Pro-D-AlaNH$_2$,
NAc-Sar-Gly-Val-D-alloIle-NMeTyr-Nva-Ile-Arg-ProNH-ethyl, and
NAc-Sar-Gly-Val-D-Ile-Thr-NMeNva-DLys(Ac)-Arg-ProNH-ethyl.

37. A composition comprising a pharmaceutically acceptable carrier and a compound according to claim 1 in an amount effective to inhibit angiogenesis.

38. A composition comprising a pharmaceutically acceptable carrier and a compound according to claim 1 in an amount effective to inhibit growth of tumor cells.

* * * * *

UNITED STATES PATENT AND TRADEMARK OFFICE
CERTIFICATE OF CORRECTION

PATENT NO. : 6,777,535 B1
DATED : August 17, 2004
INVENTOR(S) : Fortuna Haviv et al.

It is certified that error appears in the above-identified patent and that said Letters Patent is hereby corrected as shown below:

Column 53,
Line 65, delete "and".

Column 62,
Line 53, replace "and p1 D-leucyl." with -- and D-leucyl. --.

Column 63,
Line 66, replace "Va" with -- Val --.

Signed and Sealed this

Seventh Day of February, 2006

JON W. DUDAS
*Director of the United States Patent and Trademark Office*

SEQUENCE LISTING

```
<160> NUMBER OF SEQ ID NOS:  1

<210> SEQ ID NO 1
<211> LENGTH: 11
<212> TYPE: PRT
<213> ORGANISM: Artificial Sequence
<220> FEATURE:
<223> OTHER INFORMATION: Antiangiogenetic Peptide
<221> NAME/KEY: VARIANT
<222> LOCATION: (1)...(1)
<223> OTHER INFORMATION: Xaa = N-methylprolyl at position 1
<221> NAME/KEY: VARIANT
<222> LOCATION: (2)...(2)
<223> OTHER INFORMATION: Xaa = N-(R3)Ala, N-(R3)Gly, N-(R3)Nva,
      N-(R3)Pro, B-Ala, Asn, 4-ClPheAla, 4-CNPheAla, Gln, Glu, Gly,
      4-OHPro, 4-MePheAla, Pro, Ser, or Thr at position 2
```

```
<221> NAME/KEY: VARIANT
<222> LOCATION: (3)...(3)
<223> OTHER INFORMATION: Xaa = N-(R3)Ala, N-(R3)Gly, N-(R3)Leu,
      N-(R3)PheAla, Ala, Asn, Asp, 3-CNPheAla, 4-CNPheAla, Gln, Gly,
      Leu, Lys(Ac), 4-MePheAla, Nva, Pro, and PheAla as position 3
<221> NAME/KEY: VARIANT
<222> LOCATION: (4)...(4)
<223> OTHER INFORMATION: Xaa = N-(R3)Ala, N-(R3)Gly, N-(R3)HpheAla,
      N-(R3)Ile, N-(R3)Leu, N-(R3)Nva, N-(R3)PheAla, N-(R3)Ser,
      N-(R3)Tyr, N-(R3)Val, Ala, AlloIle, Allylgly, 2-Ambut, Asn, Asp at
      position 4
<221> NAME/KEY: VARIANT
<222> LOCATION: (4)...(4)
<223> OTHER INFORMATION: Xaa = 5-BrThiAla, 3-ClPheAla, 4-ClPheAla,
      3-CNPheAla, Cha, 3,4-diOMe-PheAla, 3-FpheAla, 4-FpheAla, Gln, Gly,
      His, HpheAla, Hser, Ile, Leu, Lys(Ac), Met, Met(O2), 4-MePheAla at
      position 4
<221> NAME/KEY: VARIANT
<222> LOCATION: (4)...(4)
<223> OTHER INFORMATION: Xaa =  1-Nal, 2-Nal, Nor, Nva, PheAla, PheGly,
      Pro, 3-PyrAla, 4-ThzAla, 2-ThiAla, Ser, Ser(Bzl), StyAla, Trp,
      Tyr, Val at position 4
<221> NAME/KEY: VARIANT
<222> LOCATION: (5)...(5)
<223> OTHER INFORMATION: Xaa = AlloIle, Chg, Gly, Ile at position 5
<221> NAME/KEY: VARIANT
<222> LOCATION: (6)...(6)
<223> OTHER INFORMATION: Xaa = N-(R3)Asp, N-(R3)Glu, N-(R3)Gly,
      N-(R3)Ser, N-(R3)Thr, N-(R3)Thr(Bzl), N-(R3)Tyr, Ala, AlloThr,
      Allylgly, Asn, Asp, Gln, Gly, His, Hser, 4-OHMePheAla, Ile,
      Lys(Ac) at position 6
<221> NAME/KEY: VARIANT
<222> LOCATION: (6)...(6)
<223> OTHER INFORMATION: Xaa = Met, 2-Nal, Nva, Octylgly, Pro,3-PyrAla,
      Ser, Thr, Trp, Tyr, Tyr(Me) at position 6
<221> NAME/KEY: VARIANT
<222> LOCATION: (7)...(7)
<223> OTHER INFORMATION: Xaa = N-(R3)Ala, N-(R3)Gly, N-(R3)Ile,
      N-(R3)Leu, N-(R3)Nle, N-(R3)Nva, N-(R3)Ser, N-(R3)Thr, N-(R3)Val,
      Ala, AlloThr, Allylgly, 4-AmdPheAla, 2-Ambut, Arg, Asn at position
      7
<221> NAME/KEY: VARIANT
<222> LOCATION: (7)...(7)
<223> OTHER INFORMATION: Xaa = Cha, Gln, Gly, Hala, Hser, 4-OHPro, Leu,
      Lys(Ac), Met(O2),  Met(O),  Met, Nle, Nva, Octylgly, Orn(Isp),
      PheAla, ProGly, Ser, Thr, Trp, Tyr, and Val at position 7
<221> NAME/KEY: VARIANT
<222> LOCATION: (8)...(8)
<223> OTHER INFORMATION: N-(R3)Ala, N-(R3)Ile, N-(R3)Leu, Ala, AlloIle,
      Allylgly, Cit, Gly, Ile, Leu, Lys(Ac), Met, 1-Nal, Nva, Pro, and
      Val at position 8
<221> NAME/KEY: VARIANT
<222> LOCATION: (9)...(9)
<223> OTHER INFORMATION: Xaa = N-(R3)Arg, 4-AmIspCha, 4-AmIspPheAla,
      Arg(diethyl), Arg, Cit, Gln, 4-GuPheAla, His, Harg, Lys(Isp),
      Lys(Nic), Lys, Nor, Orn, Orn(Im), Orn(Isp), and 3-PyrAla at
      position 9
<221> NAME/KEY: VARIANT
<222> LOCATION: (10)...(10)
<223> OTHER INFORMATION: Xaa = N-(R3)Ala, N-(R3)Gly, N-(R3)Hala,
      N-(R3)Nva, 2-Ambut, 2-Amisobut, dePro, 4-OHPro, PheAla, Pro, and
      Tic at position 10
<221> NAME/KEY: VARIANT
<222> LOCATION: (11)...(11)
<223> OTHER INFORMATION: Xaa = AlaNH2, AlaNH-ethyl, AzaGlyNH2, GlyNH2,
      GlyNH-ethyl, Lys(Ac), SarNH2, and SerNH2 at position 11

<400> SEQUENCE: 1

Xaa Xaa Xaa Xaa Xaa Xaa Xaa Xaa Xaa Xaa Xaa
 1               5                  10
```